US006946450B2

(12) United States Patent
Gosselin et al.

(10) Patent No.: US 6,946,450 B2
(45) **Date of Patent: *Sep. 20, 2005**

(54) β-L-2'-DEOXY-NUCLEOSIDES FOR THE TREATMENT OF HEPATITIS B

(75) Inventors: Gilles Gosselin, Montpellier (FR); Jean-Louis Imbach, Montpellier (FR); Martin L. Bryant, Carlisle, MA (US)

(73) Assignees: Idenix Pharmaceuticals, Inc., Cambridge, MA (US); Centre National de la Recherche Scientifique, Paris (FR); L'Universite Montpellier II, Montpellier (FR)

(*) Notice: Subject to any disclaimer, the term of this patent is extended or adjusted under 35 U.S.C. 154(b) by 0 days.

This patent is subject to a terminal disclaimer.

(21) Appl. No.: 10/437,802

(22) Filed: May 13, 2003

(65) Prior Publication Data

US 2003/0220290 A1 Nov. 27, 2003

Related U.S. Application Data

(63) Continuation of application No. 10/022,148, filed on Dec. 14, 2001, now Pat. No. 6,566,344, which is a continuation of application No. 09/459,150, filed on Dec. 10, 1999, now Pat. No. 6,444,652, which is a continuation-in-part of application No. 09/371,747, filed on Aug. 10, 1999, now Pat. No. 6,395,716.

(60) Provisional application No. 60/096,110, filed on Aug. 10, 1998, and provisional application No. 60/131,352, filed on Apr. 28, 1999.

(51) Int. Cl.[7] ....................... A61K 31/70; C07H 19/073

(52) U.S. Cl. ............................. 514/50; 514/51; 514/81; 514/256; 514/262; 536/28.53

(58) Field of Search .............................. 514/45–51, 81, 514/256, 262, 261; 536/28.51–28.55

(56) References Cited

U.S. PATENT DOCUMENTS

| | | | | | |
|---|---|---|---|---|---|
| 4,916,122 | A | | 4/1990 | Chu et al. | |
| 4,957,924 | A | | 9/1990 | Beauchamp | |
| 5,149,794 | A | | 9/1992 | Yatvin et al. | |
| 5,190,926 | A | | 3/1993 | Chu et al. | |
| 5,194,654 | A | | 3/1993 | Hostetler et al. | |
| 5,223,263 | A | | 6/1993 | Hostetler et al. | |
| 5,256,641 | A | | 10/1993 | Yatvin et al. | |
| 5,411,947 | A | | 5/1995 | Hostetler et al. | |
| 5,463,092 | A | | 10/1995 | Hostetler et al. | |
| 5,539,116 | A | | 7/1996 | Liotta | |
| 5,543,389 | A | | 8/1996 | Yatvin et al. | |
| 5,543,390 | A | | 8/1996 | Yatvin et al. | |
| 5,543,391 | A | | 8/1996 | Yatvin et al. | |
| 5,554,728 | A | | 9/1996 | Basava et al. | |
| 5,559,101 | A | * | 9/1996 | Weis et al. | 514/45 |
| 5,565,438 | A | | 10/1996 | Chu | |
| 5,567,688 | A | | 10/1996 | Chu | |
| 5,587,362 | A | | 12/1996 | Chu | |
| 5,939,402 | A | * | 8/1999 | Weis et al. | 514/44 |
| 6,025,335 | A | * | 2/2000 | Weis et al. | 514/44 |
| 6,194,391 | B1 | | 2/2001 | Schinazi et al. | |
| 6,245,749 | B1 | | 6/2001 | Schinazi et al. | |
| 6,297,222 | B1 | | 10/2001 | von Borstel et al. | |
| 6,395,716 | B1 | * | 5/2002 | Gosselin et al. | 514/45 |
| 6,444,652 | B1 | * | 9/2002 | Gosselin et al. | 514/45 |
| 6,566,344 | B1 | * | 5/2003 | Gosselin et al. | 514/45 |
| 6,569,837 | B1 | * | 5/2003 | Gosselin et al. | 514/45 |

FOREIGN PATENT DOCUMENTS

| | | | | |
|---|---|---|---|---|
| CA | 2206878 | | | 3/1997 |
| EP | 0 350 287 | A2 | | 1/1990 |
| EP | 0 352 248 | A1 | * | 1/1990 |
| EP | 0 494 119 | A1 | | 7/1992 |
| EP | 0 355 131 | B1 | | 9/1996 |
| JP | 06-293645 | A | | 10/1994 |

(Continued)

OTHER PUBLICATIONS

Robins, "Selective Deoxygenation and Modification at C2' of Nucleosides," pp. 1–4 in *Nucleic Acids Research Symposium Series, vol. No. 11*, Kyoto, Japan, Nov. 24–26, 1982, A. E. Pritchard (ed.), IRL Press, Ltd., Oxford, England, 1982; see also *Chemical Abstracts, 98*, Abstract No. 107670u (1982).*

(Continued)

*Primary Examiner*—L. E. Crane
(74) *Attorney, Agent, or Firm*—Sherry M. Knowles; King & Spalding LLP

(57) ABSTRACT

This invention is directed to a method for treating a host infected with hepatitis B comprising administering an effective amount of an anti-HBV biologically active 2'-deoxy-β-L-erythro-pentofuranonucleoside or a pharmaceutically acceptable salt or prodrug thereof, wherein the 2'-deoxy-β-L-erythro-pentofuranonucleoside has the formula:

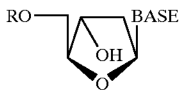

wherein R is selected from the group consisting of H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and BASE is a purine or pyrimidine base which may be optionally substituted. The 2'-deoxy-β-L-erythro-pentofuranonucleoside or a pharmaceutically acceptable salt or prodrug thereof may be administered either alone or in combination with another 2'-deoxy-β-L-erythro-pentofuranonucleoside or in combination with another anti-hepatitis B agent.

81 Claims, 4 Drawing Sheets

FOREIGN PATENT DOCUMENTS

| | | | |
|---|---|---|---|
| WO | WO 89/02733 A1 | | 4/1989 |
| WO | WO 89/03838 A1 | | 5/1989 |
| WO | WO 90/00555 A1 | | 1/1990 |
| WO | WO 91/16920 A1 | | 11/1991 |
| WO | WO 91/18914 A1 | | 12/1991 |
| WO | WO 91/19721 A1 | | 12/1991 |
| WO | WO 92/08727 A1 | | 5/1992 |
| WO | WO 92/15308 A1 | | 9/1992 |
| WO | WO 92/18517 A1 | | 10/1992 |
| WO | WO 93/00910 A1 | | 1/1993 |
| WO | WO 94/01138 A1 | | 1/1994 |
| WO | WO 94/20523 A1 | * | 9/1994 |
| WO | WO 94/26273 A1 | | 11/1994 |
| WO | WO 95/07086 A1 | | 3/1995 |
| WO | WO 96/11204 A1 | | 4/1996 |
| WO | WO 96/13512 A2 | * | 5/1996 |
| WO | WO 96/15132 A1 | | 5/1996 |
| WO | WO 96/40164 A1 | | 12/1996 |

OTHER PUBLICATIONS

Verri et al., "Relaxed Enantioselectivity of Human Mitochondrial Thymidine Kinase and Chemotherapeutic Uses of L–Nucleoside Analogues," *Biochemical Journal, 328*(1), 317–320 (Nov. 15, 1997).*

Lin et al., "Design and Synthesis of 2', 3'–Dideoxy–2', 3'–didehydro–β–L–cytidine (β–L–d4C) and 2', 3'–Dideoxy–2', 3'–didehydro–β–L–5–fluorocytidine (β–L–Fd4C), Two Exceptionally Potent Inhibitors of Human Hepatitis B Virus (HBV) and Potent Inhibitors of Human Immunodeficiency Virus (HIV) In Vitro, " *Journal of Medicinal Chemistry, 39*(9), 1757–1759 (Apr. 26, 1996).* von Janta–Lipinski et al., "Newly Synthesized L–Enantiomers of 3'–Fluoro–Modified β–2'–Deoxyribonucleoside 5'–Triphosphates Inhibit Hepatitis B DNA Polymerase But Not the Five Cellular DNA Polymerases α, β, γ, δ, and ϵ Nor HIV–1 Reverse Transcriptase," *Journal of Medicinal Chemistry, 41*(12), 2040–2046 (Jun. 4, 1996).*

Mansour et al., "Stereochemical Aspects of the Anti–HCMV Activity of Cytidine Nucleoside Analogues," *Antiviral Chemistry & Chemotherapy, 6*(3), 138–142 (1995).*

Spadari et al., "L–Thymidine Is Phosphorylated by Herpes Simplex Type 1 Thymidine Kinase and Inhibits Viral Growth," *Journal of Medicinal Chemistry, 35*(22), 4214–4220 (1992).*

Bryant et al., "Antiviral L–Nucleosides Specific for Hepatitis B Virus Infection," *Antimicrobial Agents and Chemotherapy, 45*(1), 229–235 (Jan., 2001).*

Farci et al., "Treatment of Chronic Hepatitis D with Interferon Alfa–2a," *The New England Journal of Medicine, 330*, 88–94 (Jan. 13, 1994).††*

Fujimori et al., "Enantio–oligodeoxyribonucleotides," *Symposium on Nucleic Acids Technology, Nucleic Acids Research Symposium Series, 22*, 97–98 (1990).*

Arner, E.S.J., et al., "Mammalian Deoxyribonicleoside Kinases," *Pharm. Ther.*, 67(2), 155–186 (1995).

Berk, A.J., et al., "A Genetically Distinct Tymidine Kinase in Mammalian Mitochondria," *J Biol Chem*, 248(8):2722–2729 (1973). (Apr. 25, 1973).

Bestwick, R.K., et al., "Selective Expansion of Mitochondrial Nucleoside Triphosphate Pools in Antimetabolite–treated HeLa Cells," *J. Biol. Chem.*, 257(16):9300–9304 (1982). (Aug. 25, 1982).

Bloch, A., et al. "The Role Of The 5'–Hydroxyl Group Of Adenosine In Determining Substrate Specificity For Adenosine Deaminase," *J. Med. Chem.*, 10(5):908–912 (Sep. 1967).

Bridges, E.G., et al., "Characterization of a dCTP Transport Activity Reconstituted from Human Mitochrondria," *J. Biol. Chem.*, 274(8):4620–4625 (Feb. 19, 1999).

Bridges, E.G., et al., "Identification of a novel mitochondrial dNTP carrier and its interaction with anti–HIV nucleoside analogs," *Proc. Am. Assoc. Cancer Res.*, 38:414 (Mar. 1997).

Bridges, E.G., et al., "Inhibition of Mammalian DNA Polymerase–Associated 3' to 5' Exonuclease Activity by 5'–Monophosphates of 3'–Azido–3'–Deoxythymine and 3'–Amino–3'–Deoxythymidine," *Biochemical Pharmacology*, 45(8):1571–1576 (1993).

Chang, C.N., et al., "Deoxycytidine Deaminase–resistant Stereoisomer is the Active Form of (–)–2',3'–thiacytidine in the Inhibition of Hepatitis B Virus Replication," *Journal of Biological Chemistry*, 267(20):13938–13942 (Jul. 15, 1992).

Chang, C.–N., et al., "Biochemical Pharmacology of (+)– and (–)–2',3'–Dideoxy–3'–thiacytidine as Anti–hepatitis B Virus Agents," *J Biol Chem, 267*(31), 22414–22420 (Nov. 5, 1992).

Chariot, P., et al., "Zidovudine–induced mitochondrial disorder with massive liver steatosis myopathy, lactic acidosis, and mitochondrial DNA depletion," *J. Hepatology*, 30:156–160 (1999).

Chen, M.S., et al., "Characterization of Pyrimidine Deoxyribonucleoside Kinase (Thymidine Kinase) and Thymidylate Kinase as Multifunctional Enzyme in Cells Transformed by Herpes Simplex Virus Type 1 and in Cells Infected with Mutant Strains of Herpes Simplex Virus," *J Virol.*, 30(3):942–945 (Jun. 1979).

Chen, C.–H., et al., "Delayed Cytotoxicity and Selective Loss of Mitochondrial DNA in Cells Treated with the Anti–human Immunodeficiency Virus Compound 2',3'–Dideoxycytidine," *J. Biol. Chem.*, 264(20):11934–11937 (Jul. 15, 1989).

Chen, C.–H., et al., "The Role of Cytoplasmic Deoxycytidine Kinase in the Mitochondrial Effects of the Anti–human Immunodeficiency Virus Compound 2',3'–Dideoxycytine," *J. Biol. Chem.*, 267(5):2856–2859 (Feb. 15, 1992).

Cui, L., et al., "Effect of Nucleoside Analogs on Neurite Regeneration and Mitochondrial DNA Synthesis in PC–12 Cells," *J. of Pharmacology and Experimental Therapeutics*, 280(3):1228–1234 (1997).

Davis, A.F., et al., "In Situ Localization of Mitochondrial DNA Replication in Intact Mammalian Cells," *J Cell Biol*, 135(4), 883–893 (Nov. 1996).

Davisson, et al., "Synthesis of Nucleotide 5'–Diphosphates from 5'–O–Tosyl Nucleosides," *J. Org. Chem.*, 52(9), 1794–1801 (1987).

Doong, S.–L., et al., "Inhibition of the replication of hepatitis B virus in vitro by 2',3'–dideoxy–3'–thiacytidine and related analogues," *Proc. Natl. Acad. Sci. USA*, 88:8495–8499 (Oct. 1991).

Du, J., et al, Synthesis, "Anti–Human Immunodeficiency Virus and Anti–Hepatitis B Virus Activities of Novel Oxaselenolane Nucleosides," *J. of Med. Chem.*, (40)19:2991–2993 (Sep. 12, 1997).

Dutschman, G.E., et al., "Metabolism of 2',3'–dideoxy–2', 3'–didehydro–β–L–(–)–5–Fluorocytidine and Its Activity in Combination with Climically Approved Anti–Human Immunodeficiency Virus β–D–(+) Nucleoside Analogs In Vitro," *Antimicrobial Agents and Chemotherapy*, 42(7), 1799–1804 (Jul. 1998).

Furman, P.A., et al., "The Anti–Hepatitis B Virus Activities, Cytotoxicities, and Anabolic Profiles of the (–) and (+) Enantiomers of cis–5–Fluoro–1–[2–(Hydroxymethyl)–1, 3–oxathiolane–5–yl]–Cytosine" *Antimicrobial Agents and Chemotherapy*, 36(12):2686–2692 (Dec. 1992).

Gosselin, G., et al. "Synthesis and Antiviral Evaluation of β–L–Xylofuranosyl Nucleosides of the Five Naturally Occuring Nucleic Acid Bases", *Journal of Heterocyclic Chemistry*, 30:1229–1233 (Oct.–Nov. 1993).

Hernandez–Santiago, B., et al., "Pharmacology of β–L–Thymidine and β–L–2'–Deoxycytidine in HepG2 Cell and Primary Human Hepatocytes: Relevance to Chemotherapeutic Efficacy against Hepatitis B Virus," *Antimicrobial Agents and Chemotherapy*, 46(6), 1728–1733 (Jun. 2002).

Hoard, D.E., et al., "Conversion of Mono– and Oligodeoxyribonucleotides to 5'–Triphosphates," *J. Am. Chem. Soc.*, 87(8):1785–1788 (Apr. 20, 1965).

Holy, A., "Nucleic Acid Components and Their Analogs. CLIII. Preparation of 2'–deoxy–L–Ribonucleosides of the Pyrimidine Series," *Collect. Czech. Chem. Commun.*, 37(12):4072–4087 (Dec. 1972).

Hostetler, K.Y., et al. "Synthesis And Antiretroviral Activity Of Phospholipid Analogs Of Azidothymidine And Other Antiviral Nucleosides," *J. Biol Chem.*, 265(11):6112–6115 (Apr. 15, 1990).

Hostetler, K.Y., et al., "Greatly Enhanced Inhibition Of Human Immunodeficiency Virus Type 1 Replication In CEM And HT4–6C Cells By 3'–Deoxythymidine Diphosphate Dimyristoylglycerol, A Lipid Prodrug Of 3'–Deoxythymidine," *Antimicrob Agents Chemother.*, 36(9):2025–2029 (Sep. 1992).

Imai et al., "Studies on Phosphorylation. IV. Selective Phosphorylation of the Primary Hydroxyl Group in Nucleosides," *J. Org. Chem.*, 34(6):1547–1550 (Jun. 1969).

Jones, R.J., et al., "Mini Review: Nucleotide prodrugs," *Antiviral Research*, 27:1–17 (1995).

Jurovčik, W., et al., "Metabolism of pyrimdine L–nucleosides," *Nucleic Acids Research, 3*(8), 2143–2154 (Aug. 1976).

Korba, B.E., et al., "A cell culture assay for compounds which inhibit hepatitis B virus replication," *Antiviral Res.*, 15:217–228 (1991). (Jan., 1991).

Krayevsky, A.A., et al., "Can a Substrate Enantiomer Be a Substrate for the Same Enzyme?," *Molecular Biology*, 30(5, Part 1):585–591 (1996).

Krayevsky, A.A., et al., "Should the Asymmetry of Enzymatic Active Centers Always Correlate with the Asymmetry of their Substrates?," *J. of Bionolecular Structure & Dynamics*, 14(2):225–230 (1996).

Kucera, L.S., et al., "Novel membrane–interactive ether lipid analogs that inhibit infectious HIV–1 production and induce defective virus formation," *AIDS Res Hum Retroviruses.* 6:491–501 (Apr. 1990).

Labenz, J., et al., "Analysis of the TK Enzyme Complex Induced by HSV Types 1 and 2 by Means of Isoelectric Focusing and Polyacyrlamide Gel Electrophoresis," *Arch. Virol.*, 71:235–249 (1982).

Lin, T.–S., et al., "Synthesis and Biological Evaluation of 2',3'–Dideoxy–L–pyrimidine Nucleosides as Potential Antiviral Agents agains HIV and HBV," *J. Med. Chem.*, 37:798–803 (1994).

Lin, T.–S., et al., "Synthesis of Several Pyrimidine L–Nucleoside Analogues as Potential Antiviral Agents," *Tetrahedron Letters*, 51(4):1055–1068 (1995). (Jan. 23, 1995).

Maga, G., et al., "Lack of stereospecificity of suid pseudorabies virus thymidine kinase," *Biochem. J.*, 294(2):381–385 (Sep. 1, 1993).

Nakayama, C., et al., "Synthetic Nucleosides and Nucleotides. XX. Synthesis of Various 1–β–Xylofuranosyl–5–Alkyluracils and Related Nucleosides." *Nucleosides and Nucleotides*, 1:139–146 (1982).

Norbeck, D.W., et al., "A new 2',3'–dideoxynucleoside prototype with in vitro activity against HIV," *Tetrahedron Letters*, 30(46):6263–6266 (1989).

Pan–Zhou, X.–R., et al., "Differential Effects of Antiretroviral Nucleoside Analogs on Mitochondrial Function in HepG2 Cells," *Antimicrobial Agents and Chemotherapy*, 44(3):496–503 (Mar. 2000).

Placidi, et al., "Cellular pharmacology of β–L–thymidine and β–L–2'–deoxycytidine in HepG2 cells and primary rat, monkey and human hepatocytes," *Antivir. Ther.*, 4(Suppl.4):46–47, abstract A122 (*3rd Int. Conf. Ther. Vir. Hepatitis*) (1999). (Dec. 12–16, 1999).

Robins, M. J., et al., "Purine nucleosides. XXIX. The synthesis of 2'–deoxy–L–adenosine and 2'–deoxy–L–guanosine and their α anomers," *J. Org. Chem.*, 35(3):636–639 (Mar. 1970).

Robins, M.J., et al., "Nucleic Acid Related Compounds. 42. A General Procedure for the Efficient Deoxygenation of Secondary Alcohols. Regiospecific and Stereoselective Conversion of Ribonucleosides to 2'–Deoxynucleosides," *J. Am. Chem. Soc.*, 105:4059–4065 (1983).

Saneyoshi, M., et al., "Synthetic Nucleosides and Nucleotides. XIII. Stannic Chloride Catalyzed Ribosylation of Several 6–Substituted Purines.," *Chem. Pharm. Bull.*, 27(10):2518–2521 (1979).

Schinazi, R.F., et al., "Effect of Combinations of Acylovir with Vidarabine or its 5'–Monophosphate on Herpes Simplex Viruses in Cell Culture and in Mice," *Antimicrobial Agents and Chemotherapy*, 22(3):499–507 (Jul., 1982).

Schinazi, R.F., et al., "Selective Inhibition of Human Immunodeficiency Viruses by Racemates and Enantiomers of cis–5–Fluoro–1–[2–(Hydroxymethyl)–1, 3–Oxathiolane–5–yl] Cytosine," *Antimicrobial Agents and Chemotherapy*, 36(11):2423–2431 (Nov. 1992).

Shuto, S., et al., "A facile one–step synthesis of 5'–phosphatidylnucleosides by an enzymatic two–phase reaction," *Tetrahedron Letters*, 28(2):199–202 (1987).

Söderlund, J.C.F., "Mitochondrial versus cytosolic activities of deoxyribonucleoside salvage enzymes," in *Purine and Pyrimidine Metabolism in Man VIII*, A.Shota & M. Taylor (Eds.), Plenum Press, New York, 1995, pp. 201–204.

Tyrsted et al. "Inhibition of the synthesis of 5–phosphoribosyl–1–pyrophosphate by 3'–deoxy–adenosine and structurally related nucleoside analogs," *Biochim. Biophys. Acta.*, 155(2), 619–622 (Feb. 26, 1968).

Verri, et al., "Synthesis and antiviral evaluation of –L–xylofuranosyl nucleosides of the five naturally occurring nucleic acid bases," *J. Heterocyclic Chemistry*, 30:1229–1233 (Oct.–Nov. 1993).

Verri, A., et al., "Lack of enantiospecificity of human 2'–deoxycytidine kinase: relevance for the activation of β–L–deoxycytidine analogs as antineoplastic and antiviral agents," *Molecular Phramacology*, 51(1):132–138 (Jan. 1997).

Zedeck, M.S., et al., "Inhibition of the steroid–induced synthesis of D5–3–ketosteroid isomerase in *Pseudomonas testosterone* by a new purine deoxyribonucleoside analog: 6–chloro–8–aza–9–cyclopentylpurine," *Mol. Pharmacol.*, 3(4):386–395 (1967).

Zhang, W., et al., "Removal of Silyl Protecting Groups from Hydroxyl Functions with Ammonium Fluoride in Methanol," *Tetrahedron Letter.*, 33, 1177–1180 (1992). (Jan. 25, 1992).

Zhu, Y.–L., et al., "Inhibition of Replication of Hepatitis B Virus by Cytallene In Vitro," *Antimicrobial Agents and Chemotherapy*, 41(8):1755–1760 (Aug. 1997).

Zhu, Y.–L., et al., "Anti–Hepatitis B Virus Activity and Metabolism of 2',3'–dideoxy–2',3'–didehydro–β–L–(–)–5–Fluorocytidine," *Antimicrobial Agents and Chemotherapy*, 42(7):1805–1810 (Jul. 1998).

Zhu, C., et al., "Incorporation of Nucleoside Analogs into Nuclear or Mitochondrial DNA Is Determined by the Intracellular Phosphorylation Site," *J Biol Chem*, 275(35):26727–26731 (Sep. 1, 2000).

* cited by examiner

CONTINUED ON FIG. 1A (n=3 per drug treatment group, n=4 per placebo group, dose 10mg/kg orally once per day)

β-L-2'-DEOXY-NUCLEOSIDES FOR THE TREATMENT OF HEPATITIS B

This application is a continuation application of U.S. patent application Ser. No. 10/022,148, filed on Dec. 4, 2001, which issued as U.S. Pat. No. 6,566,344, which is a continuation of U.S. patent application Ser. No. 09/459,150 filed on Dec. 10, 1999, which issued as U.S. Pat. No. 6,444,652 which is a continuation in part of U.S. patent application Ser. No. 09/371,747 filed on Aug. 10, 1999, which issued as U.S. Pat. No. 6,395,716, which claims priority to U.S. provisional application No. 60/096,110, filed on Aug. 10, 1998 and U.S. provisional application No. 60/131,352, filed on Apr. 28, 1999.

BACKGROUND OF THE INVENTION

This invention is in the area of methods for the treatment of hepatitis B virus (also referred to as "HBV") that includes administering to a host in need thereof, either alone or in combination, an effective amount of one or more of the active compounds disclosed herein, or a pharmaceutically acceptable prodrug or salt of one of these compounds.

HBV is second only to tobacco as a cause of human cancer. The mechanism by which HBV induces cancer is unknown, although it is postulated that it may directly trigger tumor development, or indirectly trigger tumor development through chronic inflammation, cirrhosis, and cell regeneration associated with the infection.

Hepatitis B virus has reached epidemic levels worldwide. After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed.

Patients typically recover from acute hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is very similar to that of acquired immune deficiency syndrome (AIDS), which accounts for why HBV infection is common among patients with AIDS or AIDS related complex. However, HBV is more contagious than HIV.

However, more recently, vaccines have also been produced through genetic engineering and are currently used widely. Unfortunately, vaccines cannot help those already infected with HBV. Daily treatments with a-interferon, a genetically engineered protein, has also shown promise, but this therapy is only successful in about one third of treated patients. Further, interferon cannot be given orally.

A number of synthetic nucleosides have been identified which exhibit activity against HBV. The (−)-enantiomer of BCH-189, known as 3TC, claimed in U.S. Pat. No. 5,539,116 to Liotta, et al., has been approved by the U.S. Food and Drug Administration for the treatment of hepatitis B. See also EPA 0 494 119 A1 filed by BioChem Pharma, Inc.

Cis-2-hydroxymethyl-5-(5-fluorocytosin-1-yl)-1,3-oxathiolane ("FTC") exhibits activity against HBV. See WO 92/15308; Furman, et al., "The Anti-Hepatitis B Virus Activities, Cytotoxicities, and Anabolic Profiles of the (−) and (+) Enantiomers of cis-5-Fluoro-1-[2-(Hydroxymethyl)-1,3-oxathiolane-5-yl]-Cytosine" *Antimicrobial Agents and Chemotherapy*, December 1992, page 2686–2692; and Cheng, et al., *Journal of Biological Chemistry*, Volume 267(20), 13938–13942 (1992).

von Janta-Lipinski et al. disclose the use of the L-enantiomers of 3'-fluoro-modified β-2'-deoxyribonucleoside 5'-triphosphates for the inhibition of hepatitis B polymerases (J. Med. Chem., 1998, 41, 2040–2046). Specifically, the 5'-triphosphates of 3'-deoxy-3'-fluoro-β-L-thymidine (β-L-FTTP), 2',3'-dideoxy-3'-fluoro-β-L-cytidine (β-L-FdCTP), and 2',3'-dideoxy-3'-fluoro-β-L-5-methylcytidine (β-L-FMethCTP) were disclosed as effective inhibitors of HBV DNA polymerases.

WO 96/13512 to Genencor International, Inc. and Lipitek, Inc. discloses that certain L-ribofuranosyl nucleosides can be useful for the treatment of cancer and viruses. Specifically disclosed is the use of this class of compounds for the treatment of cancer and HIV.

U.S. Pat. Nos. 5,565,438, 5,567,688 and 5,587,362 (Chu, et al.) disclose the use of 2'-fluoro-5-methyl-β-L-arabinofuranolyluridine (L-FMAU) for the treatment of hepatitis B and Epstein Barr virus.

Yale University and University of Georgia Research Foundation, Inc. disclose the use of L-FddC (β-L-5-fluoro-2',3'-dideoxycytidine) for the treatment of hepatitis B virus in WO 92/18517.

The synthetic nucleosides β-L-2'-deoxycytidine (β-L-2'-dC), β-L-2'-deoxythymidine (β-L-dT) and β-L-2'-deoxyadenosine (β-L-2'-dA), are known in the art. Antonin Holy first disclosed β-L-dC and β-L-dT in 1972, "Nucleic Acid Components and Their Analogs. CLIII. Preparation of 2'-deoxy-L-Ribonucleosides of the Pyrimidine Series," *Collect. Czech. Chem. Commun.* (1972), 37(12), 4072–87. Morris S. Zedeck et al. first disclosed β-L-dA for the inhibition of the synthesis of induced enzymes in *Pseudomonas testosteroni, Mol. Phys.* (1967), 3(4), 386–95.

Certain 2'-deoxy-β-L-erythro-pentofuranonucleosides are known to have antineoplastic and selected antiviral activities. Verri et al. disclose the use of 2'-deoxy-β-L-erythro-pentofuranonucleosides as antineoplastic agents and as anti-herpetic agents (*Mol. Pharmacol. (*1997), 51(1), 132–138 and *Biochem. J.* (1997), 328(1), 317–20). Saneyoshi et al. demonstrate the use of 2'-deoxy-L-ribonucleosides as reverse transcriptase (I) inhibitors for the control of retroviruses and for the treatment of AIDS, Jpn. Kokai Tokkyo Koho JP06293645 (1994).

Giovanni et al. tested 2'-deoxy-β-L-erythro-pentofuranonucleosides against partially pseudorabies virus (PRV), *Biochem. J.* (1993), 294(2), 381–5.

Chemotherapeutic uses of 2'-deoxy-β-L-erythro-pentofuranonucleosides were studied by Tyrsted et al. (*Biochim. Biophys. Acta* (1968), 155(2), 619–22) and Bloch, et al. (*J. Med. Chem.* (1967), 10(5), 908–12).

β-L-2'-deoxythymidine (β-L-dT) is known in the art to inhibit herpes simplex virus type 1 (HSV-1) thymidine kinase (TK). Iotti et al., WO 92/08727, teaches that β-L-dT selectively inhibits the phosphorylation of D-thymidine by HSV-1 TK, but not by human TK. Spaldari et al. reported that L-thymidine is phosphorylated by herpes simplex virus type 1 thymidine kinase and inhibits viral growth, *J. Med. Chem.* (1992), 35(22), 4214–20.

In light of the fact that hepatitis B virus has reached epidemic levels worldwide, and has severe and often tragic effects on the infected patient, there remains a strong need to provide new effective pharmaceutical agents to treat humans infected with the virus that have low toxicity to the host.

Therefore, it is an object of the present invention to provide new methods and compositions for the treatment of human patients or other hosts infected with hepatitis B virus.

SUMMARY OF THE INVENTION

A method for the treatment of hepatitis B infection in humans and other host animals is disclosed that includes administering an effective amount of a biologically active 2'-deoxy-β-L-erythro-pentofuranonucleoside (referred to alternatively herein as a β-L-d-nucleoside or a β-L-2'-d-nucleoside) or a pharmaceutically acceptable salt or prodrug thereof, administered either alone or in combination, optionally in a pharmaceutically acceptable carrier. The term 2'-deoxy, as used in this specification, refers to a nucleoside that has no substituent in the 2'-position.

The disclosed 2'-deoxy-β-L-erythro-pentofuranonucleosides, or pharmaceutically acceptable prodrugs or salts or pharmaceutically acceptable formulations containing these compounds are useful in the prevention and treatment of hepatitis B infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

In one embodiment of the present invention, the 2'-deoxy-β-L-erythro-pentofuranonucleoside derivative is a compound of the formula:

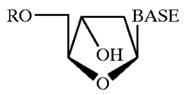

wherein R is selected from the group consisting of H, straight chained, branched or cyclic alkyl, CO-alkyl, CO-aryl, CO-alkoxyalkyl, CO-aryloxyalkyl, CO-substituted aryl, alkylsulfonyl, arylsulfonyl, aralkylsulfonyl, amino acid residue, mono, di, or triphosphate, or a phosphate derivative; and BASE is a purine or pyrimidine base which may optionally be substituted.

In another embodiment, the 2'-deoxy-β-L-erythro-pentofuranonucleoside derivative is β-L-2'-deoxyadenosine or a pharmaceutically acceptable salt or prodrug thereof, of the formula:

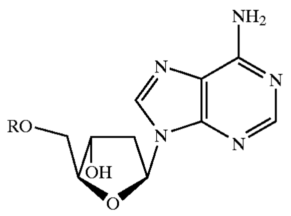

wherein R is H, mono, di or tri phosphate, amino acid residue, acyl, or alkyl, or a stabilized phosphate derivative (to form a stabilized nucleotide prodrug).

In another embodiment, the 2'-deoxy-β-L-erythro-pentofuranonucleoside derivative is β-L-2'-deoxycytidine or pharmaceutically acceptable salt or prodrug thereof of the formula:

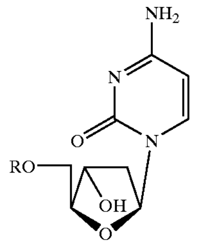

wherein R is H, mono, di or tri phosphate, amino acid residue, acyl, or alkyl, or a stabilized phosphate derivative (to form a stabilzied nucleotide prodrug).

In another embodiment, the 2'-deoxy-β-L-erythro-pentofuranonucleoside derivative is β-L-2'-deoxyuridine or pharmaceutically acceptable salt or prodrug thereof of the formula:

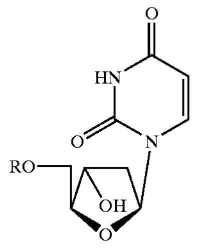

wherein R is H, mono, di or tri phosphate, amino acid residue, acyl, or alkyl, or a stabilized phosphate derivative (to form a stabilzied nucleotide prodrug).

In another embodiment, the 2'-deoxy-β-L-erythro-pentofuranonucleoside derivative is β-L-2'-deoxyguanosine or pharmaceutically acceptable salt or prodrug thereof of the formula:

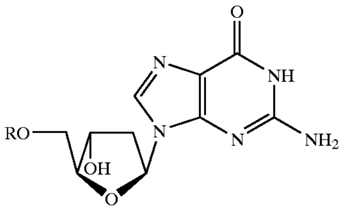

wherein R is H, mono, di or tri phosphate, amino acid residue, acyl, or alkyl, or a stabilized phosphate derivative (to form a stabilized nucleotide prodrug).

In another embodiment, the 2'-deoxy-β-L-erythro-pentofuranonucleoside derivative is β-L-2'-deoxyinosine or pharmaceutically acceptable salt or prodrug thereof of the formula:

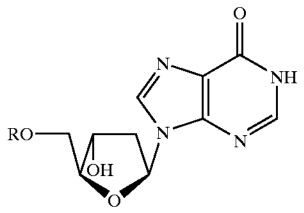

wherein R is H, mono, di or tri phosphate, amino acid residue, acyl, or alkyl, or a stabilized phosphate derivative (to form a stabilized nucleotide prodrug).

In another embodiment, the 2'-deoxy-β-L-erythro-pentofuranonucleoside derivative is β-L-thymidine or a pharmaceutically acceptable salt or prodrug thereof of the formula:

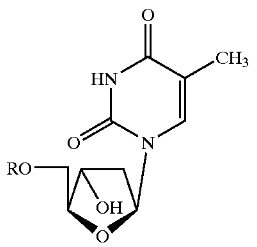

wherein R is H, mono, di or tri phosphate, amino acid residue, acyl, or alkyl, or a stabilized phosphate derivative (to form a stabilized nucleotide prodrug).

In another embodiment, the 2'-deoxy-β-L-erythro-pentofuranonucleoside is administered in alternation or combination with one or more other 2'-deoxy-β-L-erythro-pentofuranonucleosides or one or more other compounds which exhibit activity against hepatitis B virus. In general, during alternation therapy, an effective dosage of each agent is administered serially, whereas in combination therapy, an effective dosage of two or more agents are administered together. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In another embodiment, the invention includes a method for the treatment of humans infected with HBV that includes administering an HBV treatment amount of a prodrug of the disclosed 2'-deoxy-β-L-erythro-pentofuranonucleoside derivatives. A prodrug, as used herein, refers to a compound that is converted into the nucleoside on administration in vivo. Nonlimiting examples include pharmaceutically acceptable salt (alternatively referred to as "physiologically acceptable salts"), the 5' and $N^4$ (cytidine) or $N^6$ (adenosine) acylated (including with an amino acid residue such as L-valinyl) or alkylated derivatives of the active compound, or the 5'-phospholipid or 5'-ether lipids of the active compound.

DETAILED DESCRIPTION OF THE INVENTION

Figure 1:
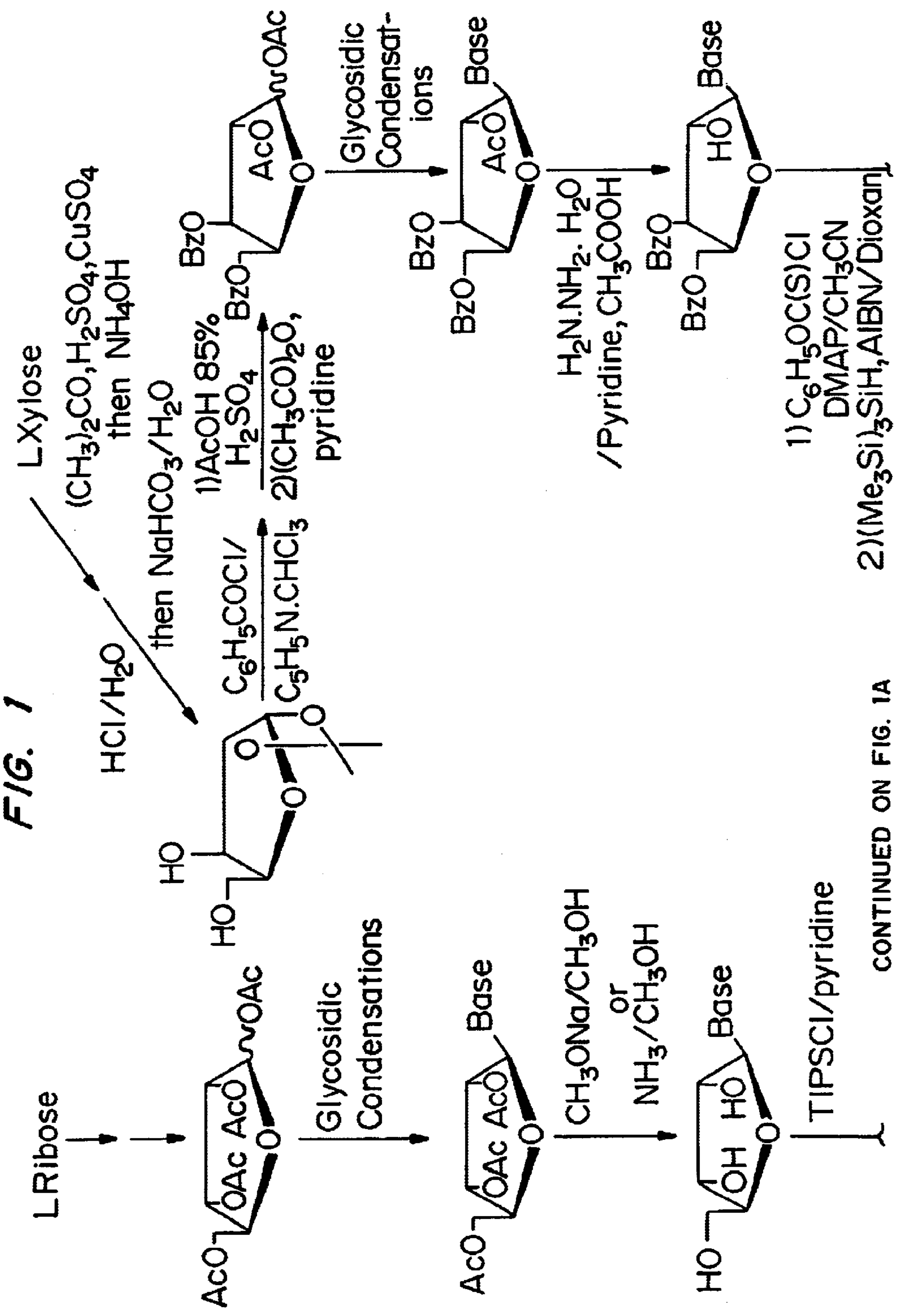
FIG. 1 illustrates a general process for obtaining β-L-erythro-pentafuranonucleosides (β-L-dN) using L-ribose or L-xylose as a starting material.
Figure 1A:
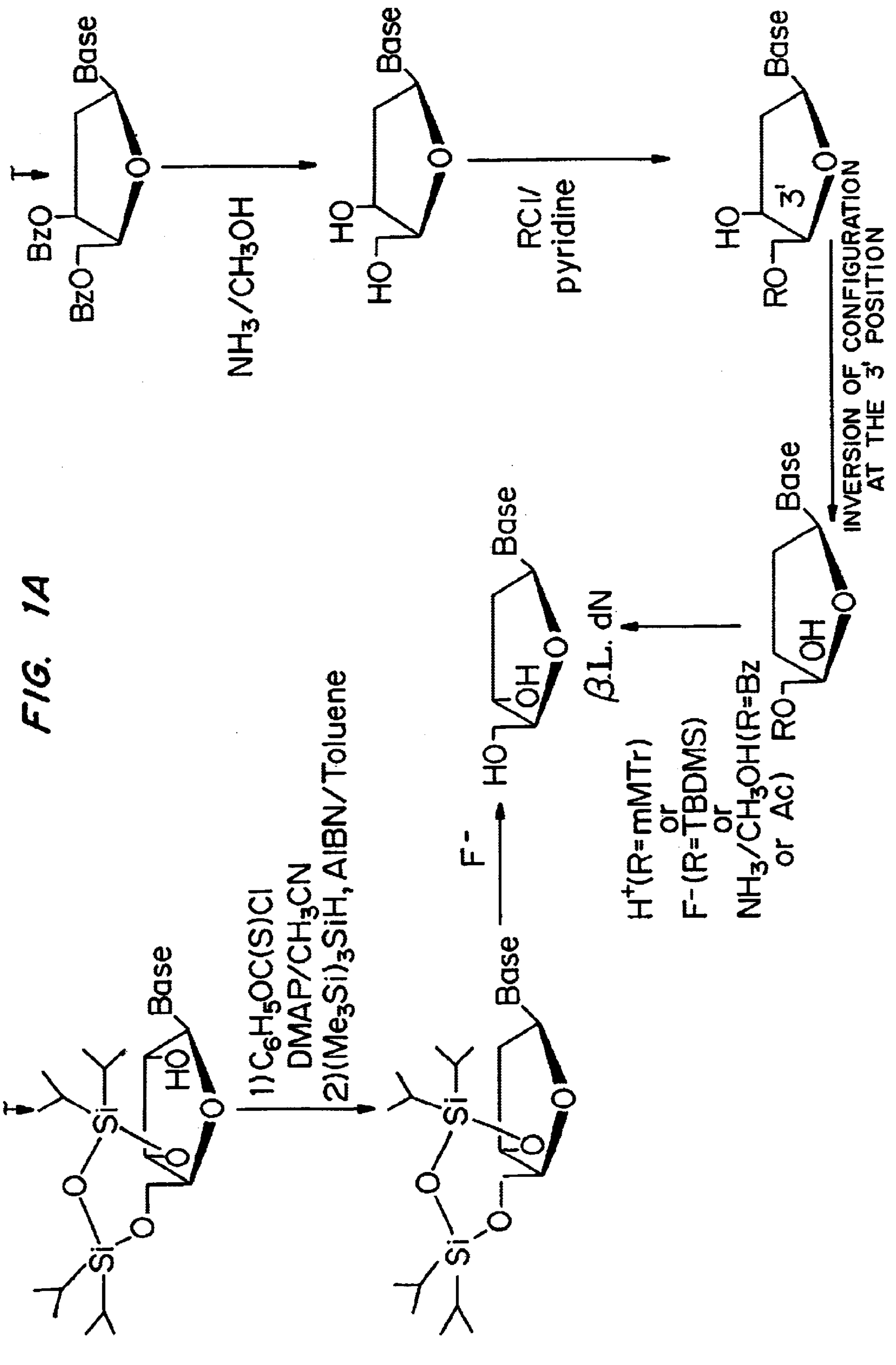
Figure 2:
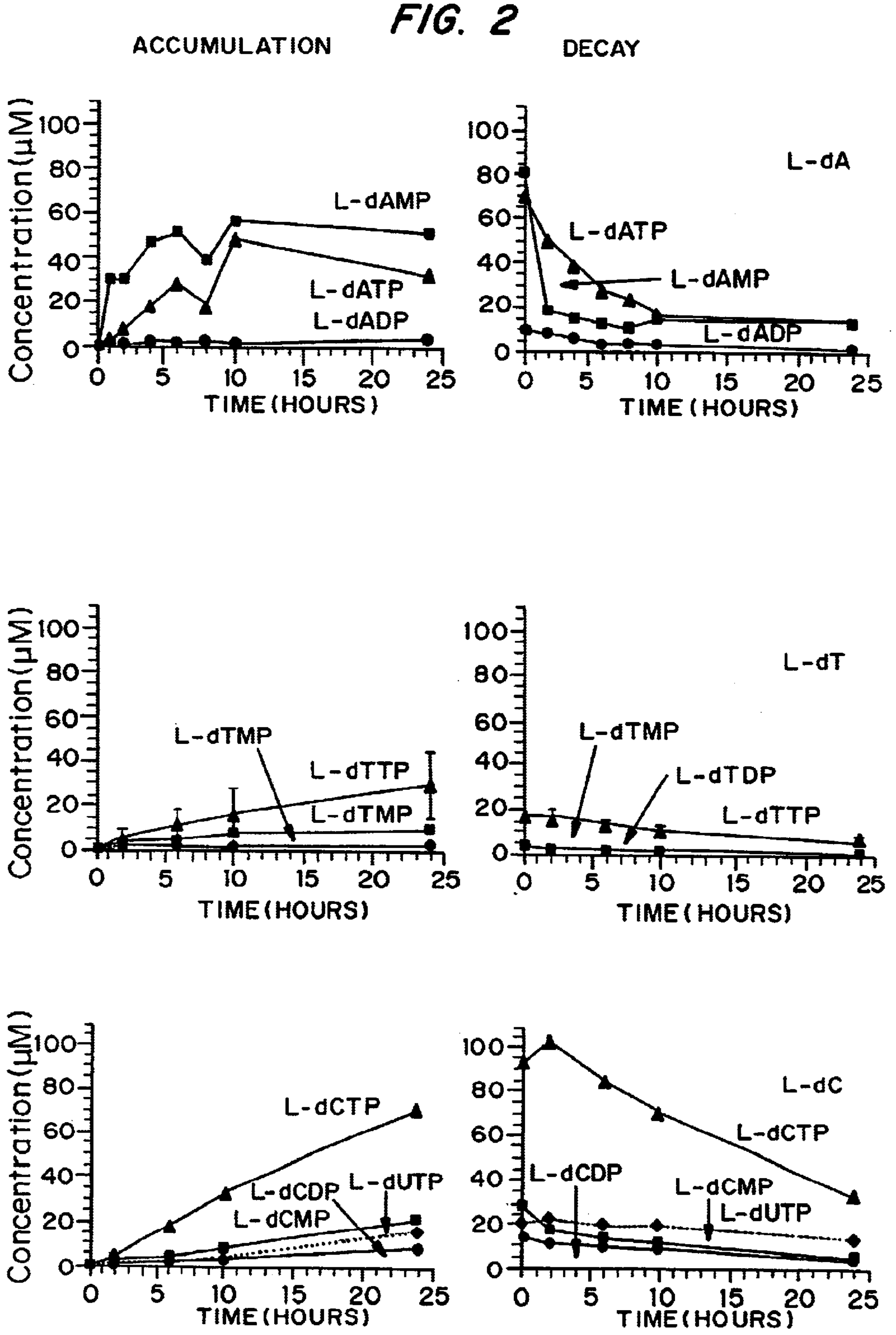
FIG. 2 is a graph which illustrates the metabolism of L-dA, L-dC, and L-dT in human Hep G2 cells in terms of accumulation and decay. The cells were incubated with 10 μM of compound.

As used herein, the term "substantially in the form of a single isomer" or "in isolated form" refers to a 2'-deoxy-β-L-erythro-pentofuranonucleoside that is at least approximately 95% in the designated stereoconfiguration. In a preferred embodiment, the active compound is administered in at least this level of purity to the host in need of therapy.

As used herein, the term hepatitis B and related conditions refers to hepatitis B and related conditions such as anti-HBV antibody positive and HBV-positive conditions, chronic liver inflammation caused by HBV, cirrhosis, acute hepatitis, fulminant hepatitis, chronic persistent hepatitis, and fatigue. The method of the present invention includes the use of 2'-deoxy-β-L-erythro-pentofuranonucleoside derivatives prophylactically to prevent or retard the progression of clinical illness in individuals who are anti-HBV antibody or HBV-antigen positive or who have been exposed to HBV.

As used herein, the term alkyl, unless otherwise specified, refers to a saturated straight, branched, or cyclic, primary, secondary, or tertiary hydrocarbon, typically of $C_1$ to $C_{18}$, preferably $C_1$ to $C_6$ and specifically includes but is not limited to methyl, ethyl, propyl, butyl, pentyl, hexyl, isopropyl, isobutyl, sec-butyl, t-butyl, isopentyl, amyl, t-pentyl, cyclopentyl, and cyclohexyl.

As used herein, the term acyl refers to moiety of the formula —C(O)R', wherein R' is alkyl; aryl, alkaryl, aralkyl, amino acid residue, heteroaromatic, alkoxyalkyl including methoxymethyl; arylalkyl including benzyl; aryloxyalkyl such as phenoxymethyl; aryl including phenyl optionally substituted with halogen, $C_1$ to $C_4$alkyl or $C_1$ to $C_4$alkoxy, or the residue of an amino acid. The term acyl specifically includes but is not limited to acetyl, propionyl, butyryl, pentanoyl, 3-methylbutyryl, hydrogen succinate, 3-chlorobenzoate, benzoyl, acetyl, pivaloyl, mesylate, propionyl, valeryl, caproic, caprylic, capric, lauric, myristic, palmitic, stearic, and oleic.

As used herein, the term purine or pyrimidine base, includes, but is not limited to, 6-alkylpurine and $N^6$-alkylpurines, $N^6$-acylpurines, $N^6$-benzylpurine, 6-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^4$-alkylpyrimidines, $N^4$-acylpyrimidines, 4-benzylpyrimidine, $N^4$-halopyrimidines, $N^4$-acetylenic pyrimidines, 4-acyl and $N^4$-acyl pyrimidines, 4-hydroxyalkyl pyrimidines, 4-thioalkyl pyrimidines, thymine, cytosine, 6-azapyrimidine, including 6-azacytosine, 2-and/or 4-mercaptopyrimidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl.

As used herein, the term amino acid residue includes but is not limited to the L or D enantiomers (or any mixture thereof, including a racemic mixture)of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl. Preferred amino acids are in the L-stereoconfiguration, and a preferred amino acid moiety is L-valinyl.

The term biologically active nucleoside, as used herein, refers to a nucleoside which exhibits an $EC_{50}$ of 15 micromolar or less when tested in 2.2.15 cells transfected with the hepatitis virion.

The term $EC_{50}$ refers to the concentration of nucleoside necessary to inhibit the replication of virus by 50%.

Preferred bases include cytosine, 5-fluorocytosine, 5-bromocytosine, 5-iodocytosine, uracil, 5-fluorouracil, 5-bromouracil, 5-iodouracil, 5-methyluracil, thymine, adenine, guanine, inosine, xanthine, 2,6-diaminopurine, 6-aminopurine, 6-chloropurine and 2,6-dichloropurine, 6-bromopurine, 2,6-dibromopurine, 6-iodopurine, 2,6-diiodopurine, 5-bromovinylcytosine, 5-bromovinyluracil, 5-bromoethenylcytosine, 5-bromoethenyluracil, 5-trifluoromethylcytosine, 5-trifluoromethyluracil.

The 2'-deoxy-β-L-erythro-pentofuranonucleoside can be provided as a 5' phospholipid or a 5'-ether lipid, as disclosed in the following references, which are incorporated by reference herein: Kucera, L. S., N. Lyer, E. Leake, A. Raben, Modest E. J., D. L. W., and C. Piantadosi. 1990. Novel membrane-interactive ether lipid analogs that inhibit infectious HIV-1 production and induce defective virus formation. AIDS Res Hum Retroviruses. 6:491–501; Piantadosi, C., J. Marasco C. J., S. L. morris-Natschke, K. L. Meyer, F. Gumus, J. R. Surles, K. S. Ishaq, L. S. Kucera, N. lyer, C. A. Wallen, S. Piantadosi, and E. J. Modest. 1991-Synthesis and evaluation of novel ether lipid nucleoside conjugates for anti-HIV activity. J Med Chem. 34:1408–1414; Hostetler, K. Y., D. D. Richman, D. A. Carson, L. M. Stuhmiller, G. M. T. van Wijk, and H. van den Bosch. 1992. Greatly enhanced inhibition of human immunodeficiency virus type 1 replication in CEM and HT4-6C cells by 31-deoxythymidine diphosphate dimyristoylglycerol, a lipid prodrug of 31-deoxythymidine. Antimicrob Agents Chemother. 36:2025–2029; Hostetler, K. Y., L. M. Stuhmiller, H. B. Lenting, H. van den Bosch, and D. D. Richman. 1990. Synthesis and antiretroviral activity of phospholipid analogs of azidothymidine and other antiviral nucleosides. J. Biol Chem. 265:6112–7.

The 2'-deoxy-β-L-erythro-pentofuranonucleoside can be converted into a pharmaceutically acceptable ester by reaction with an appropriate esterifying agent, for example, an acid halide or anhydride. The nucleoside or its pharmaceutically acceptable prodrug can be converted into a pharmaceutically acceptable salt thereof in a conventional manner, for example, by treatment with an appropriate base or acid. The ester or salt can be converted into the parent nucleoside, for example, by hydrolysis.

As used herein, the term pharmaceutically acceptable salts or complexes refers to salts or complexes of the 2'-deoxy-β-L-erythro-pentofuranonucleosides that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

The term prodrug, as used herein, refers to a compound that is converted into the nucleoside on administration in vivo. Nonlimiting examples are pharmaceutically acceptable salts (alternatively referred to as "physiologically acceptable salts"), the 5' and $N^4$ or $N^6$acylated or alkylated derivatives of the active compound, and the 5'-phospholipid and 5'-ether lipid derivatives of the active compound.

Modifications of the active compounds, specifically at the $N^4$, $N^6$ and 5'-O positions, can affect the bioavailability and rate of metabolism of the active species, thus providing control over the delivery of the active species. A preferred modification is a 5'-amino acid ester, including the L-valinyl ester.

A preferred embodiment of the present invention is a method for the treatment of HBV infections in humans or other host animals, that includes administering an effective amount of one or more of a 2'-deoxy-β-L-erythro-pentofuranonucleoside derivative selected from the group consisting of β-L-2'-deoxyadenosine, β-L-2'-deoxycytidine, β-L-2'-deoxyuridine, β-L-2'-guanosine, β-L-2'-deoxyinosine, and β-L-2'-deoxythymidine, or a physiologically acceptable prodrug thereof, including a phosphate, 5' and or $N^6$alkylated or acylated derivative, or a physiologically acceptable salt thereof, optionally in a pharmaceutically acceptable carrier. The compounds of this invention either possess anti-HBV activity, or are metabolized to a compound or compounds that exhibit anti-HBV activity. In a preferred embodiment, the 2'-deoxy-β-L-erythro-pentofuranonucleoside is administered substantially in the form of a single isomer, i.e., at least approximately 95% in the designated stereoconfiguration.

Nucleotide Prodrugs

Any of the nucleosides described herein can be administered as a stabilized nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research,* 27 (1995) 1–17. Any of these can be used in combination with the disclosed nucleosides to achieve a desired effect.

In one embodiment, the 2'-deoxy-β-L-erythro-pentofuranonucleoside is provided as 5'-hydroxyl lipophilic prodrug. Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference.

Foreign patent applications that disclose lipophilic substituents that can be attached to the 2'-deoxy-β-L-erythropentofuranonucleoside derivative of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Additional nonlimiting examples of 2'-deoxy-β-L-erythro-pentofuranonucleosides are those that contain substituents as described in the following publications. These derivatized 2'-deoxy-β-L-erythro-pentofuranonucleosides can be used for the indications described in the text or otherwise as antiviral agents, including as anti-HBV agents. Ho, D. H. W. (1973) Distribution of kinase and deaminase of 1 β-D-arabinofuranosylcytosine in tissues of man and mouse. *Cancer Res.* 33, 2816–2820; Holy, A. (1993) Isopolar phosphorous-modified nucleotide analogues. In: De Clercq (Ed.), Advances in Antiviral Drug Design, Vol. I, JAI Press, pp. 179–231; Hong, C. I., Nechaev, A., and West, C. R. (1979a) Synthesis and antitumor activity of 1□-D-arabinofuranosylcytosine conjugates of cortisol and cortisone. *Biochem. Biophys. Rs. Commun.* 88, 1223–1229; Hong, C. I., Nechaev, A., Kirisits, A. J. Buchheit, D. J. and West, C. R. (1980) Nucleoside conjugates as potential antitumor agents. 3. Synthesis and antitumor activity of 1-(β-D-arabinofuranosyl)cytosine conjugates of corticosteriods and selected lipophilic alcohols. *J. Med. Chem.* 28, 171–177; Hostetler, K. Y., Stuhmiller, L. M., Lenting, H. B. M. van den Bosch, H. and Richman, D. D. (1990) Synthesis and antiretroviral activity of phospholipid analogs of azidothymidine and other antiviral nucleosides. *J. Biol. Chem.* 265, 6112–6117; Hostetler, K. Y., Carson, D. A. and Richman, D. D. (1991); Phosphatidylazidothymidine: mechanism of antiretroviral action in CEM cells. *J. Biol. Chem.* 266, 11714–11717; Hostetler, K. Y., Korba, B. Sridhar, C., Gardener, M. (1994a) Antiviral activity of phosphatidyl-dideoxycytidine in hepatitis B-infected cells and enhanced hepatic uptake in mice. *Antiviral Res.* 24, 59–67; Hostetler, K. Y., Richman, D. D., Sridhar, C. N. Felgner, P. L, Felgner, J., Ricci, J., Gardener, M. F. Selleseth, D. W. and Ellis, M. N. (1994b) Phosphatidylazidothymidine and phosphatidyl-ddC: Assessment of uptake in mouse lymphoid tissues and antiviral activities in human immunodeficiency virus-infected cells and in rauscher leukemia virus-infected mice. *Antimicrobial Agents Chemother.* 38, 2792–2797; Hunston, R. N., Jones, A. A. McGuigan, C., Walker, R. T., Balzarini, J., and De Clercq, E. (1984) Synthesis and biological properties of some cyclic phosphotriesters derived from 2'-deoxy-5-fluorouridine. J. Med. Chem. 27, 440–444; Ji, Y. H., Moog, C., Schmitt, G., Bischoff, P. and Luu, B. (1990); Monophosphoric acid diesters of 7β-hydroxycholesterol and of pyrimidine nucleosides as potential antitumor agents: synthesis and preliminary evaluation of antitumor activity. *J. Med. Chem.* 33, 2264–2270; Jones, A. S., McGuigan, C., Walker, R. T., Balzarini, J. and DeClercq, E. (1984) Synthesis, properties, and biological activity of some nucleoside cyclic phosphoramidates. *J. Chem. Soc.* Perkin Trans. I, 1471–1474; Juodka, B. A. and Smart, J. (1974) Synthesis of ditribonucleoside a(P→N) amino acid derivatives. Coll. Czech. Chem. Comm. 39, 363–968; Kataoka, S., Imai, J., Yamaji, N., Kato, M., Saito, M., Kawada, T. and Imai, S. (1989) Alkylated cAMP derivatives; selective synthesis and biological activities. *Nucleic Acids Res. Sym. Ser.,* 21, 1–2; Kataoka, S., Uchida, R. and Yamaji, N. (1991) A convenient synthesis of adenosine 3',5' cyclic phosphate (cAMP) benzyl and methyl triesters. *Heterocycles* 32, 1351–1356; Kinchington, D., Harvey, J. J., O'Connor, T. J., Jones, B. C. N. M., Devine, K. G., Taylor-Robinson, D., Jeffies, D. J. and McGuigan, C. (1992) Comparison of antiviral effects of zidovudine phosphoramidate and phosphorodiamidate derivatives against HIV and MuLV in vitro. Antiviral Chem. Chemother. 3, 107–112; Kodama, K., Morozumi, M., Saitoh, K. I., Kuninaka, H., Yoshino, H. and Saneyoshi, M. (1989) Antitumor activity and pharmacology of 1-β-D-arabinofuranosylcytosine-5'-stearylphosphate; an orally active derivative of 1-β-D-arabinofuranosylcytosine. Jpn. J. Cancer Res. 80, 679–685; Korty, M. and Engels, J. (1979) The effects of adenosine- and guanosine 3',5'-phosphoric and acid benzyl esters on guinea-pig ventricular myocardium. Naunyn-Schmiedeberg's Arch. Pharmacol. 310, 103–111; Kumar, A., Goe, P. L., Jones, A. S. Walker, R. T. Balzarini, J. and De Clercq, E. (1990) Synthesis and biological evaluation of some cyclic phosphoramidate nucleoside derivatives. *J. Med. Chem.* 33, 2368–2375; LeBec, C., and Huynh-Dinh, T. (1991) Synthesis of lipophilic phosphate triester derivatives of 5-fluorouridine and arabinocytidine as anticancer prodrugs. *Tetrahedron Lett.* 32, 6553–6556; Lichtenstein, J., Barner, H. D. and Cohen, S. S. (1960) The metabolism of exogenously supplied nucleotides by *Escherichia coli., J. Biol. Chem.* 235, 457–465; Lucthy, J., Von Daeniken, A., Friederich, J. Manthey, B., Zweifel, J., Schlatter, C. and Benn, M. H. (1981) Synthesis and toxicological properties of three naturally occurring cyanoepithioalkanes. Mitt. Geg. Lebensmittelunters. *Hyg.* 72, 131–133 (*Chem. Abstr.* 95, 127093); McGuigan, C. Tollerfield, S. M. and Riley, P. A. (1989) Synthesis and biological evaluation of some phosphate triester derivatives of the anti-viral drug Ara. *Nucleic Acids Res.* 17, 6065–6075; McGuigan, C., Devine, K. G., O'Connor, T. J., Galpin, S. A., Jeffries, D. J. and Kinchington, D. (1990a) Synthesis and evaluation of some novel phosphoramidate derivatives of 3'-azido-3'-deoxythymidine (AZT) as anti-HIV compounds. *Antiviral Chem. Chemother.* 1, 107–113; McGuigan, C., O'Connor, T. J., Nicholls, S. R. Nickson, C. and Kinchington, D. (1990b) Synthesis and anti-HIV activity of some novel substituted dialkyl phosphate derivatives of AZT and ddCyd. *Antiviral Chem. Chemother.* 1, 355–360; McGuigan, C., Nicholls, S. R., O'Connor, T. J., and Kinchington, D. (1990c) Synthesis of some novel dialkyl phosphate derivative of 3'-modified nucleosides as potential anti-AIDS drugs. *Antiviral Chem. Chemother.* 1, 25–33; McGuigan, C., Devine, K. G., O'Connor, T. J., and Kinchington, D.(1991) Synthesis and anti-HIV activity of some haloalkyl phosphoramidate derivatives of 3'-azido-3'-deoxythymidine (AZT); potent activity of the trichloroethyl methoxyalaninyl compound. *Antiviral Res.* 15, 255–263; McGuigan, C., Pathirana, R. N., Mahmood, N., Devine, K. G. and Hay, A. J. (1992) Aryl phosphate derivatives of AZT retain activity against HIV-1 in cell lines which are resistant to the action of AZT. *Antiviral Res.* 17, 311–321; McGuigan, C., Pathirana, R. N., Choi, S. M., Kinchington, D. and O'Connor, T. J. (1993a) Phosphoramidate derivatives of AZT as inhibitors of HIV; studies on the carboxyl terminus. *Antiviral Chem. Chemother.* 4, 97–101; McGuigan, C., Pathirana, R. N., Balzarini, J. and De Clercq, E. (1993b) Intracellular delivery of bioactive AZT nucleotides by aryl phosphate derivatives of AZT. *J. Med. Chem.* 36, 1048–1052.

The question of chair-twist equilibria for the phosphate rings of nucleoside cyclic 3',5'-monophosphates. $^1$HNMR and x-ray crystallographic study of the diasteromers of thymidine phenyl cyclic 3',5'-monophosphate. *J. Am. Chem. Soc.* 109, 4058–4064; Nerbonne, J. M., Richard, S., Nargeot, J. and Lester, H. A. (1984) New photoactivatable cyclic nucleotides produce intracellular jumps in cyclic AMP and cyclic GMP concentrations. *Nature* 301, 74–76; Neumann, J. M., Hervé, M., Debouzy, J. C., Guerra, F. I., Gouyette, C., Dupraz, B. and Huynh-Dinh, T. (1989) Synthesis and transmembrane transport studies by NMR of a glucosyl phospholipid of thymidine. *J. Am. Chem. Soc.* 111, 4270–4277;

Ohno, R., Tatsumi, N., Hirano, M., Imai, K. Mizoguchi, H., Nakamura, T., Kosaka, M., Takatuski, K., Yamaya, T., Toyama, K., Yoshida, T., Masaoka, T., Hashimoto, S., Ohshima, T., Kimura, I., Yamada, K. and Kimura, J. (1991) Treatment of myelodysplastic syndromes with orally administered 1-β-D-rabinofuranosylcytosine-5'-stearylphosphate. *Oncology* 48, 451–455.

Palomino, E., Kessle, D. and Horwitz, J. P. (1989) A dihydropyridine carrier system for sustained delivery of 2',3'-dideoxynucleosides to the brain. *J. Med. Chem.* 32, 622–625; Perkins, R. M., Barney, S., Wittrock, R., Clark, P. H., Levin, R. Lambert, D. M., Petteway, S. R., Serafinowska, H. T., Bailey, S. M., Jackson, S., Harnden, M. R. Ashton, R., Sutton, D., Harvey, J. J. and Brown, A. G. (1993) Activity of BRL47923 and its oral prodrug, SB203657A against a rauscher murine leukemia virus infection in mice. *Antiviral Res.* 20 (Suppl. I). 84; Piantadosi, C., Marasco, C. J., Jr., Morris-Natschke, S. L., Meyer, K. L., Gumus, F., Surles, J. R., Ishaq, K. S., Kucera, L. S. Iyer, N., Wallen, C. A., Piantadosi, S. and Modest, E. J. (1991) Synthesis and evaluation of novel ether lipid nucleoside conjugates for anti-HIV-1 activity. *J. Med. Chem.* 34, 1408–1414; Pompon, A., Lefebvre, I., Imbach, J. L., Kahn, S. and Farquhar, D. (1994) Decomposition pathways of the mono- and bis (pivaloyloxymethyl) esters of azidothymidine-5'-monophosphate in cell extract and in tissue culture medium; an application of the 'on-line ISRP-cleaning' HPLC technique. *Antiviral Chem. Chemother.* 5, 91–98; Postemark, T. (1974) Cyclic AMP and cyclic GMP. *Annu. Rev. Pharmacol.* 14, 23–33; Prisbe, E. J., Martin, J. C. M., McGee, D. P. C., Barker, M. F., Smee, D. F. Duke, A. E., Matthews, T. R. and Verheyden, J. P. J. (1986) Synthesis and antiherpes virus activity of phosphate and phosphonate derivatives of 9-[(1, 3-dihydroxy-2-propoxy)methyl] guanine. *J. Med. Chem.* 29, 671–675; Puech, F., Gosselin, G., Lefebvre, I., Pompon, A., Aubertin, A. M. Dim, A. and Imbach, J. L. (1993) Intracellular delivery of nucleoside monophosphate through a reductase-mediated activation process. *Antiviral Res.* 22, 155–174; Pugaeva, V. P., Klochkeva, S. I., Mashbits, F. D. and Eizengart, R. S. (1969). Robins, R. K. (1984) The potential of nucleotide analogs as inhibitors of retroviruses and tumors. *Pharm. Res.* 11–18; Rosowsky, A., Kim. S. H., Ross and J. Wick, M. M. (1982) Lipophilic 5'-(alkylphosphate) esters of 1-β-D-arabinofuranosylcytosine and its $N^4$-acyl and 2.2'-anhydro-3'-O-acyl derivatives as potential prodrugs. *J. Med. Chem.* 25, 171–178; Ross, W. (1961) Increased sensitivity of the walker turnout towards aromatic nitrogen mustards carrying basic side chains following glucose pretreatment. *Biochem. Pharm.* 8, 235–240; Ryu, E. K., Ross, R. J. Matsushita, T., MacCoss, M., Hong, C. I. and West, C. R. (1982). Phospholipid-nucleoside conjugates. 3. Synthesis and preliminary biological evaluation of 1-β-D-arabinofuranosylcytosine 5'diphosphate[−], 2-diacylglycerols. *J. Med. Chem.* 25, 1322–1329; Saffhill, R. and Hume, W. J. (1986) The degradation of 5-iododeoxyuridine and 5-bromodeoxyuridine by serum from different sources and its consequences for the use of these compounds for incorporation into DNA. *Chem. Diol. Interact.* 57, 347–355; Saneyoshi, M., Morozumi, M., Kodama, K., Machida, J., Kuninaka, A. and Yoshino, H. (1980) Synthetic nucleosides and nucleotides. XVI. Synthesis and biological evaluations of a series of 1-β-D-arabinofuranosylcytosine 5'-alkyl or arylphosphates. *Chem. Pharm. Bull.* 28, 2915–2923; Sastry, J. K., Nehete, P. N., Khan, S., Nowak, B. J., Plunkett, W., Arlinghaus, R. B. and Farquhar, D. (1992) Membrane-permeable dideoxyuridine 5'-monophosphate analogue inhibits human immunodeficiency virus infection. *Mol. Pharmacol.* 41, 441–445; Shaw, J. P., Jones, R. J. Arimilli, M. N., Louie, M. S., Lee, W. A. and Cundy, K. C. (1994) Oral bioavailability of PMEA from PMEA prodrugs in male Sprague-Dawley rats. 9th Annual AAPS Meeting. San Diego, Calif. (Abstract). Shuto, S., Ueda, S., Imamura, S., Fukukawa, K. Matsuda, A. and Ueda, T. (1987) A facile one-step synthesis of 5'-phosphatidylnucleosides by an enzymatic two-phase reaction. *Tetrahedron Lett.* 28, 199–202; Shuto, S., Itoh, H., Ueda, S., Imamura, S., Kukukawa, K., Tsujino, M., Matsuda, A. and Ueda, T. (1988) A facile enzymatic synthesis of 5'-(3-sn-phosphatidyl)nucleosides and their antileukemic activities. *Chem. Pharm. Bull.* 36, 209–217. One preferred phosphate prodrug group is the S-acyl-2-thioethyl group, also referred to as "SATE."

Combination or Alternation Therapy

It has been recognized that drug-resistant variants of HBV can emerge after prolonged treatment with an antiviral agent. Drug resistance most typically occurs by mutation of a gene that encodes for an enzyme used in the viral life cycle, and most typically in the case of HBV, DNA polymerase. Recently, it has been demonstrated that the efficacy of a drug against HBV infection can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

The anti-hepatitis B viral activity of β-L-2'-dA, β-L-2'-dC, β-L-2'-dU, β-L-2'-dG, β-L-2'-dT, β-L-dI, or other β-L-2'-nucleosides provided herein, or the prodrugs, phosphates, or salts of these compounds, can be enhanced by administering two or more of these nucleosides in combination or alternation. Alternatively, for example, one or more of β-L-2'-dA, β-L-2'-dC, β-L-2'-dU, β-L-2'-dG, β-L-2'-dT, β-L-dI, or other β-L-2'-nucleosides provided herein can be administered in combination or alternation with 3TC, FTC, L-FMAU, DAPD, famciclovir, penciclovir, BMS-200475, bis pom PMEA (adefovir, dipivoxil); lobucavir, ganciclovir, or ribavarin.

In any of the embodiments described herein, if the β-L-2'-nucleoside of the present invention is administered in combination or alternation with a second nucleoside or nonnucleoside reverse transcriptase inhibitor that is phosphorylated to an active form, it is preferred that a second compound be phosphorylated by an enzyme that is different from that which phosphorylates the selected β-L-2'-nucleoside of the present invention in vivo. Examples of kinase enzymes are thymidine kinase, cytosine kinase, guanosine kinase, adenosine kinase, deoxycytidine kinase, 5'-nucleotidase, and deoxyguanosine kinase.

Preparation of the Active Compounds

The 2'-deoxy-β-L-erythro-pentofuranonucleoside derivatives of the present invention are known in the art and can be prepared according to the method disclosed by Holy, *Collect. Czech. Chem. Commun.* (1972), 37(12), 4072–87 and *Mol. Phys.* (1967), 3(4), 386–95.

A general process for obtaining β-L-erythro-pentofuranonucleosides (β-L-dN) is shown in FIG. 1, using L-ribose or L-xylose as a starting material.

Mono, di, and triphosphate derivatives of the active nucleosides can be prepared as described according to published methods. The monophosphate can be prepared according to the procedure of Imai et al., *J. Org. Chem.,* 34(6), 1547–1550 (June 1969). The diphosphate can be prepared according to the procedure of Davisson et al., *J. Org. Chem.,* 52(9), 1794–1801 (1987). The triphosphate can be prepared according to the procedure of Hoard et al., *J. Am. Chem. Soc.,* 87(8), 1785–1788 (1965).

Experimental Protocols

Melting points were determined in open capillary tubes on a Gallenkamp MFB-595-010 M apparatus and are uncorrected. The UV absorption spectra were recorded on an Uvikon 931 (KONTRON) spectrophotometer in ethanol. $^1H$-NMR spectra were run at room temperature in DMSO-$d_6$ with a Bruker AC 250 or 400 spectrometer. Chemical shifts are given in ppm, DMSO-$_{d_5}$ being set at 2.49 ppm as reference. Deuterium exchange, decoupling experiments or 2D-COSY were performed in order to confirm proton assignments. Signal multiplicities are represented by s (singlet), d (doublet), dd (doublet of doublets), t (triplet), q (quadruplet), br (broad), m (multiplet). All J-values are in Hz. FAB mass spectra were recorded in the positive-(FAB>0) or negative-(FAB<0) ion mode on a JEOL DX 300 mass spectrometer The matrix was 3-nitrobenzyl alcohol (NBA) or a mixture (50:50, v/v) of glycerol and thioglycerol (GT). Specific rotations were measured on a Perkin-Elmer 241 spectropolarimeter (path length 1 cm) and are given in units of $10^{-1}$ deg cm$^2$ g$^{-1}$. Elemental analysis were carried out by the "Service de Microanalyses du CNRS, Division de Vernaison" (France). Analyses indicated by the symbols of the elements or functions were within ±0.4% of theoretical values. Thin layer chromatography was performed on precoated aluminium sheets of Silica Gel 60 $F_{254}$ (Merck, Art. 5554), visualisation of products being accomplished by UV absorbency followed by charring with 10% ethanolic sulfuric acid and heating. Column chromatography was carried out on Silica Gel 60 (Merck, Art. 9385) at atmospheric pressure.

EXAMPLE 1

Stereospecific Synthesis of 2'-Deoxy-β-L-Adenosine 9-(3,5-Di-O-benzoyl-β-L-xylofuranosyl)adenine (3)

A solution of 9-(2-O-acetyl-3,5-di-O-benzoyl-β-L-xylofuranosyl)adenine 2 [Ref.: Gosselin, G.; Bergogne, M. -C.; Imbach, J. -L., "Synthesis and Antiviral Evaluation of β-L-Xylofuranosyl Nucleosides of the Five Naturally Occuring Nucleic Acid Bases", *Journal of Heterocyclic Chemistry,* 1993, 30 (October–November), 1229–1233] (8.30 g, 16.05 mmol) and hydrazine hydrate 98% (234 mL, 48.5 inmol) in a mixture of pyridine/glacial acetic acid (4/1, v/v, 170 mL) was stirred at room temperature for 22 h. The reaction was quenched by adding acetone (40 mL) and stirring was continued for one additional hour. The reaction mixture was reduced to one half of its volume, diluted with water (250 mL) and extracted with chloroform (2×150 mL). The organic layer was washed successively with an aqueous saturated solution of $NaHCO_3$ (3×100 mL) and water (3×100 mL), dried, filtered, concentrated and co-evaporated with toluene and methanol. The residue was purified by silica gel column chromatography (0–3% MeOH in dichloromethane) to give 3 (5.2 g, 68%) precipitated from diisopropylic ether: $^1H$ NMR (DMSO-$d_6$): δ 4.5–4.9 (m, 4H, H-2', H-4', H-5' and H-5"), 5.64 (t, 1H, H-3', $J_{2',3'}$=$J_{3',4'}$=3.5 Hz), 6.3 (br s, 1H, OH-2'), 6.45 (d, 1H, H-1', $J_{1',2'}$=4.6 Hz), 7.3 (br s, 2H, $NH_2$-6), 7.4–7.9 (m, 10H, 2 benzoyls), 8.07 and 8.34 (2s, 2H, H-2 and H-8); ms: matrix G/T, (FAB$^+$) m/z 476 $[M+H]^+$, 136 $[BH_2]^+$, (FAB$^-$) m/z 474 $[M-H]^-$, 134 $[B]^-$; UV (95% ethanol): $\lambda_{max}$ 257 nm (ε 16400), 230 nm (ε 29300), $\lambda_{max}$ 246 nm (ε 14800); $[\alpha]_D^{20}$=−64 (c 1.07, $CHCl_3$). Anal. Calcd for $C_{24}H_{21}N_5O_4$ (M=475.45): C, 60.43; H, 4.45; N, 14.73. Found: C, 60.41; H, 4.68; N, 14.27.

9-(3,5-Di-O-benzoyl-2-deoxy-β-L-threo-pentofuranosyl) adenine (4).

To a solution of compound 3 (1.00 g, 2.11 mmol) in dry acetonitrile (65 mL) were added 4-(dimethylamino)pyridine (0.77 g, 6.32 mmol) and phenoxythiocarbonyl chloride (0.44 mL, 3.16 mmol). The mixture was stirred at room temperature for 2 h. After concentration, the residue was dissolved in dichloromethane (50 mL) and washed successively with water (2×30 mL), aqueous solution of hydrochloric acid 0.5 N (30 mL) and water (3×30 mL). The organic layer was dried, filtered and concentrated to dryness. The crude thiocarbonylated intermediate was directly treated with tris-(trimethylsilyl)silane hydride (0.78 mL, 5.23 mmol) and α,α'-azoisobutyronitrile (AIBN, 0.112 g, 0.69 mmol) in dry dioxane (17 mL) at reflux for 2 h. The solvent was removed under vacuum and the residue was purified by silica gel column chromatography (0–5% MeOH in dichloromethane) to give pure 4 (0.93 g, 96%) as a foam: $^1H$ NMR (DMSO-$d_6$): δ 2.9–3.1 (m, 2H, H-2' and H-2"), 4.6–4.7 (m, 3H, H-4', H-5' and H-5"), 5.8 (br s, 1H, H-3'), 6.43 (dd, 1H, H-1', $J_{1',2'}$=3.1 Hz, $J_{1',2''}$=7.6 Hz), 7.3 (br s, 2H, $NH_2$-6), 7.4–7.9 (m, 10H, 2 benzoyls), 8.05 and 8.33 (2s, 2H, H-2 and H-8); ms: matrix G/T, (FAB$^+$) m/z 460 $[M+H]^+$, 325 $[S]^+$, 136 $[BH_2]^+$, (FAB$^-$) m/z 458 $[M-H]^-$; 134 $[B]^-$; UV (95% ethanol): $\lambda_{max}$ 261 nm (ε 14400), 231 nm (ε 26300), $\lambda_{min}$ 249 nm (ε 12000); $[\alpha]_D^{20}$=−38 (c 1.04, DMSO).

6-N-(4-Monomethoxytrityl)-9-(3,5-di-O-benzoyl-2-deoxy-β-L-threo-pento-furanosyl)adenine (5).

To a solution of compound 4 (0.88 g, 1.92 mmol) in dry pyridine (40 mL) was added 4-monomethoxytrityl chloride (1.18 g, 3.84 mmol). The mixture was stirred at 60° C. for 24 h. After addition of methanol (5 mL), the solution was concentrated to dryness, the residue was dissolved in dichloromethane (50 mL) and washed successively with water (30 mL), aqueous saturated $NaHCO_3$ (30 mL) and water (30 mL). The organic layer was dried, filtered, concentrated and co-evaporated with toluene to give pure 5 (1.01 g, 72%) as a foam: $^1H$ NMR ($CDCl_3$): δ 2.9–3.0 (m, 2H, H-2' and H-2"), 3.62 (s, 3H, $OCH_3$), 4.6–4.8 (m, 3H, H-4', H-5' and H5"), 5.85 (pt, 1H, H-3'), 6.44 (dd, 1H, H-1', $J_{1',2'}$=3.1 Hz, $J_{1',2''}$=7.3 Hz), 6.9 (br s, 1H, NH-6), 6.7–6.8 and 7.2–7.4 (2m, 24H, 2 benzoyls and MMTr), 7.97 and 8.13 (2s, 2H, H-2 and H-8); ms: matrix G/T, (FAB$^+$) m/z 732 $[M+H]^+$, (FAB$^-$) m/z 730 $[M-H]^-$; UV (95% ethanol): $\lambda_{max}$ 274 nm (ε 12100), 225 nm (ε 24200), $\lambda_{min}$ 250 nm (ε 5900); $[\alpha]_D^{20}$=−16 (c 1.12, DMSO).

6-N-(4-Monomethoxytrityl)-9-(2-deoxy-β-L-threo-pentofuranosyl)-adenine (6).

Compound 5 (0.95 g, 1.30 mmol) was treated with a solution (saturated at −10° C.) of methanolic ammonia (40 mL), at room temperature overnight. After concentration, the residue was dissolved in dichloromethane (60 mL) and washed with water (30 mL). The aqueous layer was extracted twice with dichloromethane (10 mL). The combined organic layer was dried, filtered and concentrated. The residue was purified by silica gel column chromatography (0–5% MeOH in dichloromethane) to give pure 6 (0.67 g, 98%) as a foam: $^1H$ NMR ($CDCl_3$): δ 2.6–2.9 (m, 2H, H-2' and H-2"), 3.5 (br s, 1H, OH-5'), 3.55 (s, 3H, $OCH_3$), 3.9–4.0 (m, 3H, H-4', H-5' and H-5"), 4.5–4.6 (m, 1H, H-3'), 6.03 (dd, 1H, H-1', $J_{1',2'}$=4.0 Hz, $J_{1',2''}$=8.8 Hz), 7.0 (br s, 1H, NH-6), 6.7–6.8 and 7.1–7.4 (2m, 14H, MMTr), 7.40 (d, 1H, OH-3', $J_{H,OH}$ =10.6 Hz), 7.80 and 7.99 (2s, 2H, H-2 and H-8); ms: matrix G/T, (FAB$^+$) m/z 524 $[M+H]^+$, 408 $[BH_2]^+$, (FAB$^-$), m/z 1045 $[2M-H]^-$, 522 $[M-H]^-$, 406 $[B]^-$; UV (95% ethanol): $\lambda_{max}$ 275 nm (ε 12300), $\lambda_{min}$ 247 nm (ε 3600); $[\alpha]_D^{20}$=+28 (c 0.94, DMSO).

6-N-(4-Monomethoxytrityl)-9-(2-deoxy-5-O-(4-monomethoxytrityl)-β-L-threo-pentofuranosyl)adenine (7).

Compound 6 (0.62 g, 1.24 mmol) in dry pyridine (25 mL) was treated with 4-monomethoxytrityl chloride (0.46 g, 1.49 mmol) at room temperature for 16 h. After addition of methanol (5 mL), the mixture was concentrated to dryness. The residue was dissolved in dichloromethane (60 mL) and washed successively with water (40 mL), a saturated aqueous solution of $NaHCO_3$ (40 mL) and water (3×40 mL). The organic layer was dried, filtered, concentrated and co-evaporated with toluene and methanol. The residue was purified by silica gel column chromatography (0–10% MeOH in dichloromethane) to give 7 (0.71 g, 72%) as a foam: $^1H$ NMR (DMSO-$d_6$): δ 2.21 (d, 1H, H-2' $J_{2',2''}$=14.3 Hz), 2.6–2.7 (m, 1H, H-2"), 3.1–3.3 (2m, 2H, H-5' and H-5"), 3.64 and 3.65 (2s, 6H, 2×$OCH_3$), 4.1–4.2 (m, 1H, H-4'), 4.2–4.3 (m, 1H, H-3'), 5.68 (d, 1H, OH-3', $J_{H,OH}$=5.2 Hz), 6.24 (d, 1H, H-1', $J_{1',2''}$=7.0 Hz), 6.7–6.8 and 7.1–7.3 (2m, 29H, 2 MMTr and NH-6), 7.83 and 8.21 (2s, 2H, H-2 and H-8); m: matrix G/T, ($FAB^+$) m/z 796 $[M+H]^+$, 408 $[BH_2]^+$, ($FAB^-$) m/z 794 $[M-H]^-$, 406 $[B]^-$; UV (95% ethanol): $\lambda_{max}$ 275 nm (ϵ 30900), $\lambda_{min}$ 246 nm (ϵ 12800); $[\alpha]_D^{20}$=+14 (c 1.03, DMSO).

6-N-(4-Monomethoxytrityl)-9-(3-O-benzoyl-2-deoxy-5-O-(4-mono-methoxytrityl)-β-L-erythro-pentofuranosyl) adenine (8).

A solution of diethylazodicarboxylate (0.38 mL, 2.49 mmol) in dry tetrahydrofuran (20 mL) was added dropwise to a cooled solution (0° C.) of nucleoside 7 (0.66 g, 0.83 mmol), triphenylphosphine (0.66 g, 2.49 mmol) and benzoic acid (0.30 g, 2.49 mmol) in dry THF (20 mL). The mixture was stirred at room temperature for 18 h and methanol (1 mL) was added. The solvents were removed under reduced pressure and the crude material was purified by silica gel column chromatography (0–5% ethyl acetate in dichloromethane) to give compound 8 slightly contaminated by triphenylphosphine oxide.

6-N-(4-Monomethoxytrityl)-9-(2-deoxy-5-O-(4-monomethoxytrityl)-β-L-erythro-pentofuranosyl)adenine (9).

Compound 8 was treated by a solution (saturated at −10° C.) of methanolic ammonia (20 mL), at room temperature for 24 h, then the reaction mixture was concentrated to dryness. The residue was dissolved in dichloromethane (30 mL) and washed with water (20 mL). The aqueous layer was extracted by dichloromethane (2×20 mL) and the combined organic phase was dried, filtered and concentrated. Pure compound 9 (0.50 g, 76% from 7) was obtained as a foam after purification by silica gel column chromatography (0–2% MeOH in dichloromethane): $^1H$ NMR (DMSO-$d_6$): δ 2.2–2.3 (m, 1H, H-2'), 2.8–2.9 (m, 1H, H-2"), 3.1–3.2 (m, 2H, H-5' and H-5"), 3.64 and 3.65 (2s, 6H, 2×$OCH_3$), 3.97 (pq, 1H, H-4'), 4.4–4.5 (m, 1H, H-3'), 5.36 (d, 1H, OH-3', $J_{H,OH}$=4.5 Hz), 6.34 (t, 1H, H-1', $J_{1',2'}$=$J_{1',2''}$=6.4 Hz), 6.8–6.9 and 7.1–7.4 (2m, 29H, 2 MMTr and NH-6), 7.81 and 8.32 (2s, 2H, H-2 and H-8); ms: matrix G/T, ($FAB^+$) m/z 796 $[M+H]^+$, 408 $[BH_2]^+$, ($FAB^-$) m/z 794 $[M-H]^-$, 406 $[B]^-$; UV (95% ethanol): $\lambda_{max}$ 276 nm (ϵ 42600), $\lambda_{min}$ 248 nm (ϵ 23300); $[\alpha]_D^{20}$=+29 (c 1.05, DMSO).

2'-Deoxy-β-L-adenosine (β-L-dA)

Compound 9 (0.44 g, 0.56 mmol) was treated with an aqueous solution of acetic acid 80% (17 mL) at room temperature for 5 h. The mixture was concentrated to dryness, the residue was dissolved in water (20 mL) and washed with diethyl ether (2×15 mL). The aqueous layer was concentrated and co-evaporated with toluene and methanol. The desired 2'-deoxy-β-L-adenosine (β-L-dA) (0.12 g, 83%) was obtained after purification by silica gel column chromatography (0–12% MeOH in dichloromethane) and filtration through a Millex HV-4 unit (0.45 μ, Millipore): mp 193–194° C. (crystallized from water) (Lit. 184–185° C. for L-enantiomer [Ref.: Robins, M. J.; Khwaja, T. A.; Robins, R. K. *J. Org. Chem.* 1970, 35, 636–639] and 187–189° C. for D-enantiomer [Ref.: Ness, R. K. in *Synthetic Procedures in Nucleic Acid Chemistry*; Zorbach, W. W., Tipson, R. S., Eds.; J. Wiley and sons: New York, 1968; Vol 1, pp 183–187]; $^1H$ NMR (DMSO-$d_6$): δ 2.2–2.3 and 2.6–2.7 (2m, 2H, H-2' and H-2"), 3.4–3.6 (2m, 2H, H-5' and H-5"), 3.86 (pq, 1H, H-4'), 4.3–4.4 (m, 1H, H-3'), 5.24 (t, 1H, OH-5', $J_{H,OH}$=5.8 Hz), 5.30 (d, 1H, OH-3', $J_{H,OH}$=4.0Hz), 6.32 (dd, 1H, H-1', $J_{1',2'}$=6.2Hz, $J_{1',2''}$=7.8 Hz), 7.3 (br s, 2H, $NH_2$-6), 8.11 and 8.32 (2s, 2H, H-2 and H-8); ms: matrix G/T, ($FAB^+$) m/z 252 $[M+H]^+$, 136 $[BH_2]^+$, ($FAB^-$) m/z 250 $[M-H]^-$, 134 $[B]^-$; UV (95% ethanol): $\lambda_{max}$ 258 nm (ϵ 14300), $\lambda_{min}$ 226 nm (ϵ 2100); $[\alpha]_D^{20}$=+25 (c 1.03, $H_2O$), (Lit. $[\alpha]_D^{20}$=+23 (c 1.0, $H_2O$) for L-enantiomer [Ref.: Robins, M. J.; Khwaja, T. A.; Robins, R. K. *J. Org. Chem.* 1970, 35, 636–639] and $[\alpha]_D^{20}$=−25 (c 0.47, $H_2O$) for D-enantiomer [Ref.: Ness, R. K. in *Synthetic Procedures in Nucleic Acid Chemistry*; Zorbach, W. W., Tipson, R. S., Eds.; J. Wiley and sons: New York, 1968; Vol 1, pp 183–187]). Anal. Calcd for $C_{10}H_{13}N_5O_3$+1.5 $H_2O$ (M=278.28): C, 43.16; H, 5.80; N, 25.17. Found: C, 43.63; H, 5.45; N, 25.33.

EXAMPLE 2

Stereoselective Synthesis of 2'-Deoxy-β-L-Adenosine (β-L-dA)

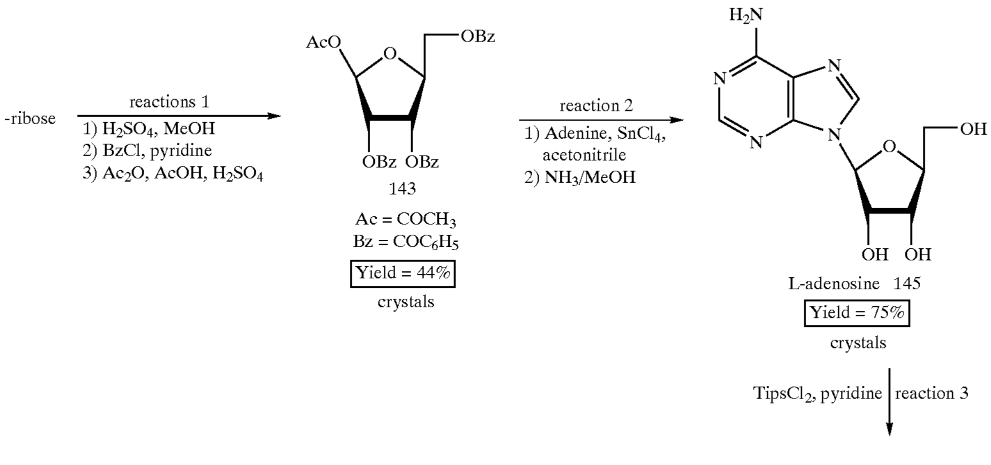

-continued

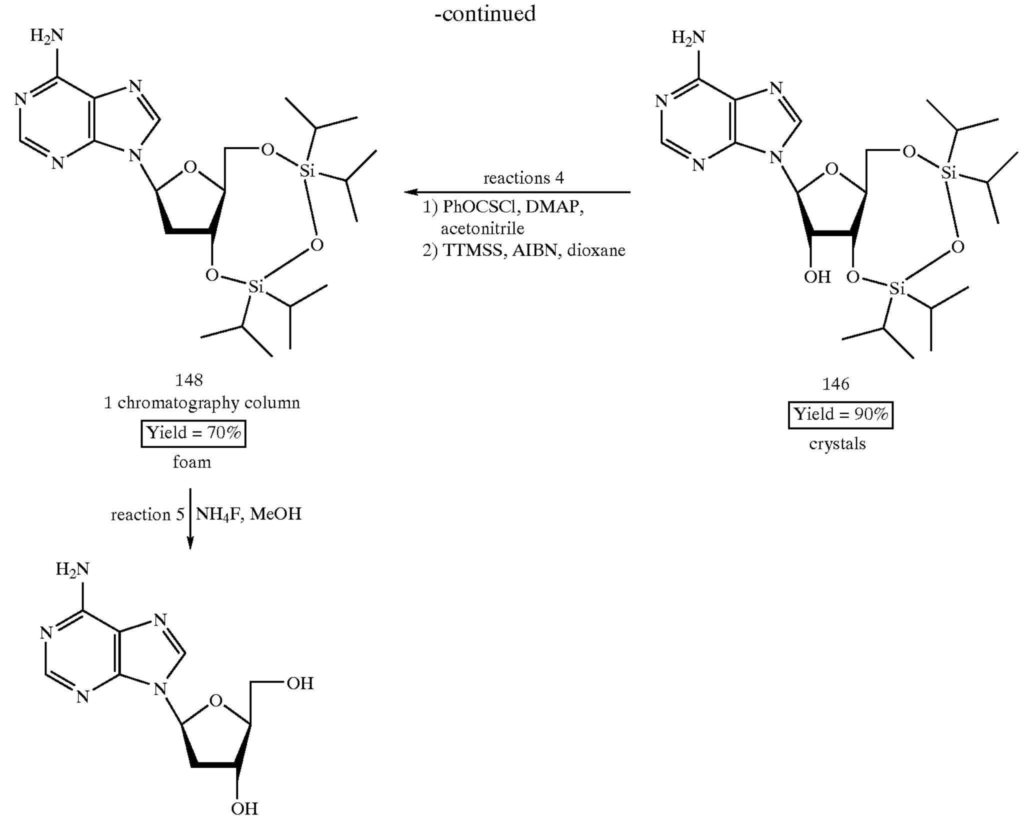

L-deoxyadenosine 149
1 chromatography column
Yield - 75%
crystals

Reaction 1:

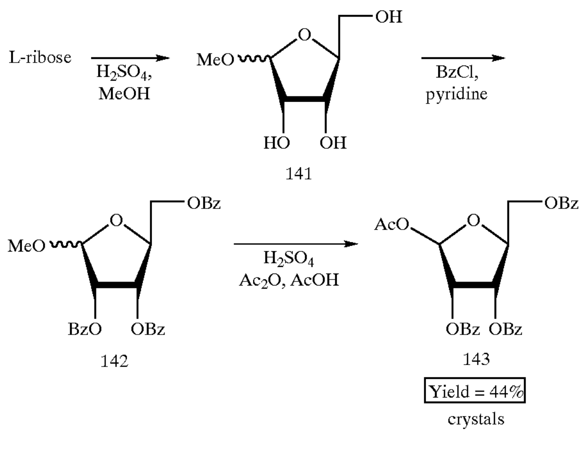

Precursor: L-ribose (Cultor Science Food, CAS [24259-59-4], batch RIB9711013)

Reactants: Sulphuric acid 95–97% (Merck; ref 1.00731.1000); Benzoyl chloride (Fluka; ref 12930); Sodium sulfate (Prolabo; ref 28111.365)

Solvents: Methanol P.A. (Prolabo; ref 20847.295); Pyridine 99% (Acros; ref 131780025); Dichloromethane P.A. (Merck; ref 1.06050.6025); Acetic acid P.A. (carlo erba; ref 20104298); Acetic anhydride (Fluka; ref 45830); Ethanol 95 (Prolabo; ref 20823.293)

References: Recondo, E. F., and Rinderknecht, H., Eine neue, Einfache Synthese des 1-O-Acetyl-2,3,5-Tri-O-β-D-Ribofuranosides. *Helv. Chim. Acta,* 1171–1173 (1959).

A solution of L-ribose 140 (150 g, 1 mol) in methanol (2 liters) was treated with sulphuric acid (12 ml) and left at +4° C. for 12 hrs, and then neutralised with pyridine (180 ml). Evaporation gave an α,β mixture of methyl ribofuranosides 141 as a syrup. A solution of this anomeric mixture in pyridine (1.3 liters) was treated with benzoyl chloride (580 ml, 5 mol) with cooling and mechanical stirring. The solution was left at room temperature for 12 hrs and then poured on ice (about 10 liters) with continued stirring. The mixture (an oil in water) was filtered on a Cellite bed. The resulting oil on the cellite bed was washed with water (3x3 liters) and then dissolved with ethyl acetate (3 liters). The organic phase was washed with a 5% $NaHCO_3$ solution (2 liters) and water (2 liters), dried over sodium sulfate, filtered and evaporated to give 1-O-methyl-2,3,5-tri-O-benzoyl-α/β-L-ribofuranose 142 as a thick syrup. The oil was dissolved in acetic anhydride (560 ml) and acetic acid (240 ml). The solution was, after the dropwise addition of concentrated sulphuric acid (80 ml), kept in the cold (+4° C.) under mechanical stirring for 10 hrs. The solution was then poured on ice (about 10 liters) under continued stirring. The mixture (oily compound in water) was filtered on a Cellite bed. The resulting gummy solid on the cellite bed was washed with water (3x3 liters) and then dissolved in dichloromethane (2,5 liters). The organic phase was washed with 5% $NaHCO_3$ (1 liter) and water (2x2 liters), dried over sodium sulfate, filtered and evaporated to give a gummy solid 143, which was crystallized from ethanol 95 (yield 225 g, 44%).

Analyses for 1-O-acetyl-2,3,5-tri-O-benzoyl-β-L-ribofuranose 143:

mp 129–130° C. (EtOH 95) (lit.(1) mp 130–131° C.) $^1$H NMR (200 MHz, $CDCl_3$): δ8.09–7.87 (m, 6H, $H_{Arom}$), 7.62–7.31 (m, 9H, $H_{Arom}$) 6.43 (s, 1H, $H_1$), 5.91 (dd, 1H, $H_3$, $J_{3,4}$ 6.7 Hz; $J_{3,2}$ 4.9 Hz), 5.79 (pd, 1H, $H_2$, $J_{2,3}$ 4.9 Hz; $J_{1,2}$<1), 4.78 (m, 2H, $H_4$ and $H_5$), 4.51 (dd, 1H, $H_5$, $J_{5,5'}$13.1 Hz, $J_{5',4}$ 5.5 Hz), 2.00 (s, 3H, $CH_3CO$), (identical to commercial 1-O-acetyl-2,3,5-tri-O-benzoyl-β-D-ribofuranose) Mass analysis (FAB+, GT) m/z 445 $(M-OAc)^+$ Elemental analysis $C_{28}H_{24}O_9$ Calculated C 66.66 H 4.79; found C H Reaction 2:

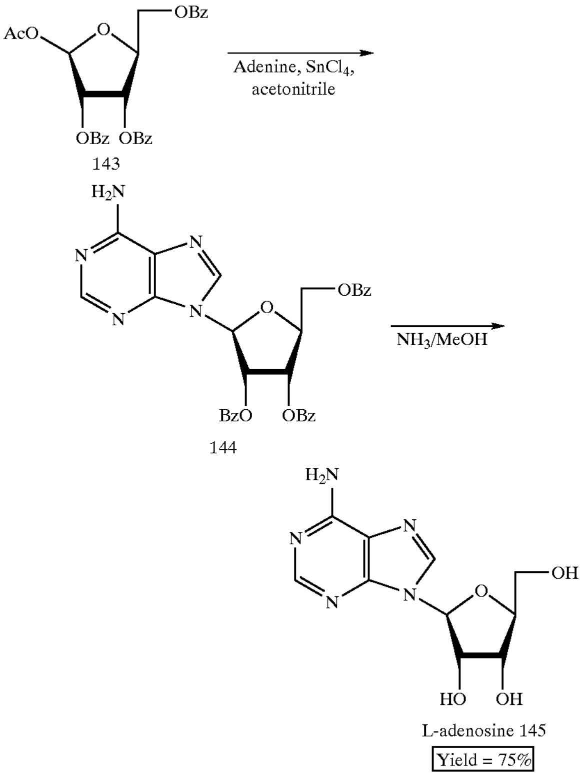

143

144

L-adenosine 145

Yield = 75% crystals

Precursor: Adenine (Pharma-Waldhof; ref 400134.001 lot 45276800)

Reactants: Stannic chloride fuming (Fluka; ref 96558); $NH_3$/Methanol (methanol saturated with $NH_3$; see page 5); Sodium sulfate (Prolabo; ref 28111.365)

Solvents: Acetonitrile (Riedel-de Hean; ref 33019; distilled over $CaH_2$); Chloroform Pur (Acros; ref 22706463); Ethyl acetate Pur (Carlo erba; ref 528299)

References: Saneyoshi, M., and Satoh, E., Synthetic Nucleosides and Nucleotides. XIII. Stannic Chloride Catalyzed Ribosylation of Several 6-Substituted Purines. *Chem; Pharm. Bull.,* 27, 2518–2521 (1979).; Nakayama, C., and Saneyoshi, M., Synthetic Nucleosides and Nucleotides. XX. Synthesis of Various 1-β-Xylofuranosyl-5-Alkyluracils and Related Nucleosides. *Nucleosides, Nucleotides,* 1, 139–146 (1982).

Adenine (19.6 g, 144 mmol) was suspended in acetonitrile (400 ml) with 1-O-acetyl-2,3,5-tri-O-benzoyl-β-L-ribofuranose 143 (60 g, 119 mmol). To this suspension was added stannic chloride filming (22 ml, 187 mmol). After 12 hrs, the reaction was concentrated to a small volume (about 100 ml), and sodium hydrogencarbonate (110 g) and water (120 ml) were added. The resulting white solid (tin salts)

was extracted with hot chloroform (5×200 ml). The combined extracts were filtered on a cellite bed. The organic phase was washed with a $NaHCO_3$ 5% solution and water, dried over sodium sulfate, filtered and evaporated to give compound 144 (60 g, colorless foam). The foam was treated with methanol saturated with ammonia (220 ml) in sealed vessel at room temperature under stirring for 4 days. The solvent was evaporated off under reduced pressure and the resulting powder was suspended in ethyl acetate (400 ml) at reflux for 1 hr. After filtration, the powder was recrystallized from water (220 ml) to give L-adenosine 145 (24 g, crystals, 75%)

Analyses for β-L-adenosine:

mp 233–234° C. (water) (lit.(4) mp 235°-238° C.) $^1$H NMR (200 MHz, DMSO-$D_6$): δ8.34 and 8.12 (2s, 2H, $H_2$ and $H_8$), 7.37 (1s, 2H, $NH_2$), 5.86 (d, 1H, $H_{1'}$, $J_{1'2'}$6.2 Hz), 5.43 (m, 2H, $OH_{2'}$ and $OH_{5'}$), 5.19 (d, 1H, $OH_{3'}$, J 3.7 Hz), 4.60 (m, $H_{2'}$), 4.13 (m, 1H, $H_{3'}$), 3.94 (m, 1H, $H_{4'}$) 3.69–3.49 (m, 2H, $H_{5'a}$ and $H_{5'b}$), (identical to commercial D-adenosine) Mass analysis (FAB+, GT) m/z 268 $(M+H)^+$, $136(BH_2)^+$ Reaction 3:

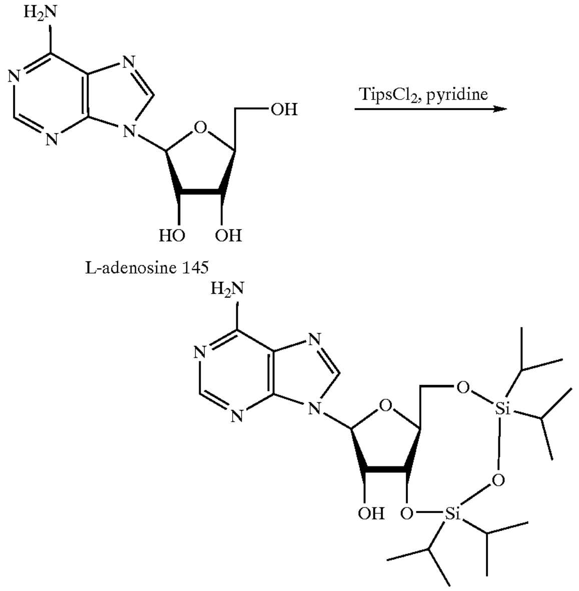

L-adenosine 145

146

Yield = 90% crystals

Reactants: 1,3-Dichloro-1,1,3,3-tetraisopropyldisiloxane (Fluka; ref 36520); Sodium sulfate (Prolabo; ref 28111.365)

Solvents: Pyridine 99% (Acros; ref 131780025); Ethyl acetate Pur (Carlo erba; ref 528299); Acetonitrile (Riedel-de Haen; ref 33019)

Reference: Robins, M. J., et al., Nucleic Acid Related Compounds. 42. A General Procedure for the Efficient Deoxygenation of Secondary Alcohols. Regiospecific and Stereoselective Conversion of Ribonucleosides to 2'-Deoxynucleosides. *J. Am. Chem. Soc.* 105, 4059–4065 (1983).

To L-adenosine 145 (47.2 g, 177 mmol) suspended in pyridine (320 ml) was added 1,3-dichloro-1,1,3,3-tetraisopropyldisiloxane (63 ml, 201 mmol), and the mixture was stirred at room temperature for 12 hrs. Pyridine was evaporated and the residue was partitioned with ethyl acetate (1 liter) and a $NaHCO_3$ 5 % solution (600 ml). The organic phase was washed with a HCl 0.5N solution (2×500 ml) and water (500 ml), dried over sodium sulfate, filtered and evaporated to dryness. The resulting solid was crystallized from acetonitrile to give compound 146 (81 g, 90%).

Analyses 3',5'-O-(1,1,3,3-tetraisopropyl-1,3-disiloxanyl)-β-L-adenosine 146:

mp 97–98° C. (acetonitrile) (lit. (5) D enantiomer mp 98° C.) $^1$H NMR (200 MHz, $CDCl_3$): δ8.28 and 7.95 (2s, 2H, $H_2$ and $H_8$), 5.96 (d, 1H, $J_{1',2'}$1.1 Hz), 5.63 (s, 2H, $NH_2$), 5.10 (dd, 1H, $H_{3'}$, $J_{3',4'}$7.6 Hz, $J_{3',2'}$5.5 Hz), 4.57 (dd, 1H, $H_{2'}$, $J_{2',1'}$1.2 Hz; $J_{2',3'}$7.6 Hz), 4.15–3.99 (m, 3H, $H_{4'}$, $H_{5'a}$ and $H_{5'b}$), 3.31 (sl, 1H, $OH_{2'}$), 1.06 (m, 28H, isopropyl protons) Mass analysis (FAB−, GT) m/z 508 $(M-H)^-$, 134 $(B)^-$; (FAB+, GT) m/z 510 $(m+H)^+$, 136 $(BH_2)^+$ Reaction 4:

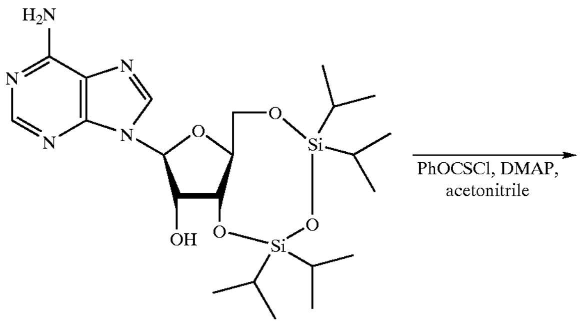

146

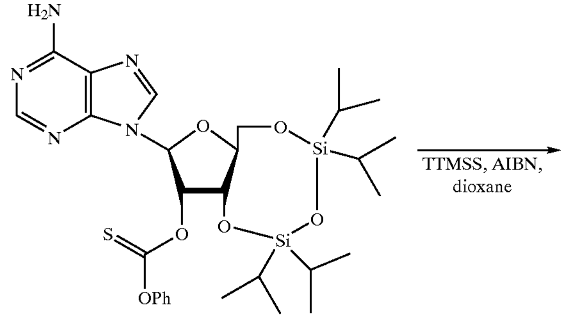

147

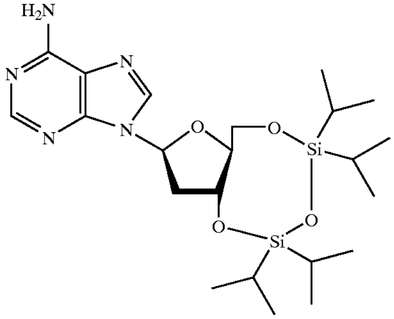

148

1 chromatography column

Yield = 70% foam

Reactants: Dimethylaminopyridine 99% (Acros; ref 1482702050); Phenylchlorothionocarbonate 99% (Acros; ref 215490050); Tris(trimethylsilyl)silane “TTMSS” (Fluka; ref 93411); α,α'-Azoisobutyronitrile “AIBN” (Fluka, ref 11630); Sodium sulfate (Prolabo; ref 28111.365)

Solvents: Acetonitrile (Riedel-de Haen; ref 33019); Ethyl acetate Pur (Carlo Erba; ref 528299); Dioxan P.A. (Merck; ref 1.09671.1000); Dichloromethane (Merck; ref 1.06050.6025); Methanol (Carlo Erba; ref 309002);

Reference: Robins, M. J., Wilson, J. S., and Hansske, F., Nucleic Acid Related Compounds. 42. A General Procedure for the Efficient Deoxygenation of Secondary Alcohols. Regiospecific and Stereoselective Conversion of Ribonucleosides to 2'-Deoxynucleosides. *J. Am. Chem. Soc.,* 105, 4059–4065 (1983).

To compound 146 (34 g, 67 mmol) were added acetonitrile (280 ml), DMAP (16.5 g, 135 mmol) and phenyl chlorothionocarbonate (10.2 ml, 73 mmol). The solution was stirred at room temperature for 12 hrs. Solvent was evaporated and the residue was partioned between ethyl acetate (400 ml) and a HCl 0.5N solution (400 ml). The organic layer was washed with a HCl 0.5N solution (400 ml) and water (2×400 ml), dried over sodium sulfate, filtered and evaporated to dryness to give the intermediate as a pale yellow solid. The crude 147 was dissolved in dioxan (ml) and AIBN (3.3 g, 20 mmol) and TTMSS (33 ml, 107 mmol) were added. The solution was progressively heated until reflux and stirred for 2 hrs. The reaction was concentrated to a yellow oil which was chromatographed (eluent dichloromethane/methanol 95/5) to give compound 148 (23 g, colorless foam, 70%). An aliquot was cristallized from ethanol/petroleum ether.

Analyses for 3',5'-O-(1,1,3,3-tetraisopropyl-1,3-disiloxanyl)-2'-deoxy-β-L-adenosine 148:

mp 110–111° C. (EtOH/petroleum ether) (Lit.(5) mp 113–114° C. (EtOH)) $^1$H NMR (200 MHz, $CDCl_3$): δ8.33 and 8.03 (2s, 2H, $H_2$ and $H_8$), 6.30 (dd, 1H, $H_{1'}$, J 2.85 Hz, J 7.06 Hz), 5.63 (sl, 2H, $NH_2$), 4.96 (m, 1H, $H_{3'}$), 4.50 (m, 2H, $H_{5'a}$ and $H_{5'b}$), 2.68 (m, 2H, $H_{2'a}$ and $H_{2'b}$), 1.08 (m, 28H, isopropyl protons) Mass analysis (FAB+, GT) m/z 494 $(M+H)^+$, 136 $(BH_2)^+$ Reaction 5:

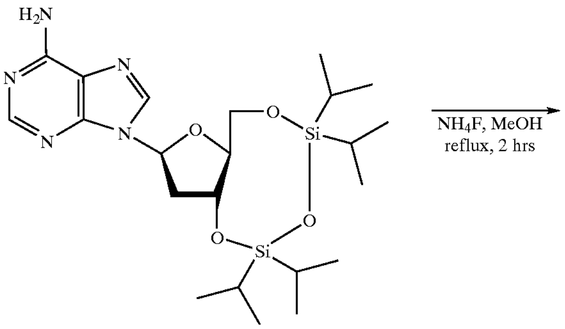

148

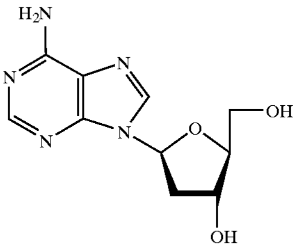

L-deoxyadenosine 149

1 chromatography column

Yield = 75% crystals

Reactants: Ammonium fluoride (Fluka; ref 09742); Silica gel (Merck; ref 1.07734.2500)

Solvents: Methanol P.A. (Prolabo; ref 20847.295); Dichloromethane P.A. (Merck; ref 1.06050.6025); Ethanol 95 (Prolabo; ref 20823.293)

Reference: Zhang, W., and Robins, M. J., Removal of Silyl Protecting Groups from Hydroxyl Functions with Ammonium Fluoride in Methanol. *Tetrahedron Lett.,* 33, 1177–1180 (192).

A solution of 3',5'-O-(1,1,3,3-tetraisopropyl-1,3-disiloxanyl)-2'-deoxy-L-adenosine 148 (32 g, 65 mmol) and ammonium fluoride (32 g, mmol) in methanol was stirred at reflux for 2 hrs. Silica gel was added and the mixture was carefully evaporated to give a white powder. This powder was added on the tpo of a silica column, which was eluted with dichloromethane/methanol 9/1. The appropriate fractions were combined and evaporated to give a white powder, which was crystallized from ethanol 95 (12.1 g, 75%).

Analyses for 2'-Deoxy-β-L-adenosine 149:

mp 189–190° C. (EtOH 95) (identical to commercial 2'-deoxy-D-adenosine) $^1$H NMR (200 MHz, DMSO-$D_6$): δ8.35 and 8.14 (2s, 2H, $H_2$ and $H_8$), 7.34 (s1, 2H, $NH_2$), 6.35 (dd, 1H, H1', J 6.1 Hz, J 7.85 Hz), 5.33 (d, 1H, $OH_{2'}$, J 4.0 Hz), 5.28 (dd, 1H, $H_{3'}$, J 4.9 Hz; J 6.6 Hz), 4.42 (m, 1H, $OH_{5'}$), 3.88 (m, 1H, $H_{4'}$), 3.63–3.52 (m, 2H, $H_{5'a}$ and $H_{5'b}$), 2.71 (m, 1H, $H_{2'a}$), 2.28 (m, 1H, $H_{2'b}$). (identical to commercial 2'-deoxy-D-adenosine) $\alpha_D$+26° (c 0.5 water) (commercial 2'-deoxy-D-adenosine −25° (c 0.5 water)). UV $\lambda_{max}$ 260 nm (ϵ 14100) ($H_2O$). Mass analysis (FAB+, GT) m/z 252 $(M+H)^+$, 136 $(BH_2)^+$

EXAMPLE 3

Stereospecific Synthesis of 2'-Deoxy-β-L-Cytidine 1-(3,5-Di-O-benzoyl-β-L-xylofuranosyl)uracil (11)

Hydrazine hydrate (1.4 mL, 28.7 mmol) was added to a solution of 1-(2-O-acetyl-3,5-di-O-benzoyl-β-L-xylofuranosyl)uracil 10 [Ref.: Gosselin, G.; Bergogne, M. -C.; Imbach, J. -L., "Synthesis and Antiviral Evaluation of β-L-Xylofuranosyl Nucleosides of the Five Naturally Occuring Nucleic Acid Bases", Journal of Heterocyclic Chemistry, 1993, 30 (October-November), 1229–1233] (4.79 g, 9.68 mmol) in pyridine (60 mL) and acetic acid (15 mL). The solution was stirred overnight at room temperature. Acetone was added (35 mL) and the mixture was stirred for 30 min. The reaction mixture was evaporated under reduced pressure. The resulting residue was purified by silica gel column chromatography [eluent: stepwise gradient of methanol (0–4%) in dichloromethane to give 11 (3.0 g, 68%) which was crystallized from cyclohexane/dichloromethane: mp=111–114° C.; $^1$H-NMR (DMSO-$d_6$): δ11.35 (br s, 1H, NH), 7.9–7.4 (m, 11H, 2 $C_6H_5CO$, H-6), 6.38 (d, 1H, OH-2', $J_{OH-2'}$=4.2 Hz), 5.77 (d, 1H, H-1', $J_{1',2'}$=1.9 Hz), 5.55 (d, 1H, H-5, $J_{5-6}$=8 Hz), 5.54 (dd, 1H, H-3', $J_{3'-2'}$=3.9 Hz and $J_{3'-4'}$=1.8 Hz), 4.8 (m, 1H, H-4'), 4.7 (m, 2H, H-5' and H-5"), 4.3 (m, 1H, H-2'); MS: FAB>0 (matrix GT) m/z 453 $(M+H)^+$, 105 $(C_6H_5CO)^+$; FAB<0 (matrix GT) m/z 451 $(M-H)^-$, 121 $(C_6H_5CO_2)^-$, 111 $(B)^-$; Anal. Calcd for $C_{23}H_{20}N_2O_8.H_2O$: C, 58.09; H, 4.76; N, 5.96. Found: C, 57.71; H, 4.42; N, 5.70.

1-(3,5-Di-O-benzoyl-β-L-arabinofuranosyl)uracil (12)

To a solution of 1-(3,5-di-O-benzoyl-β-L-xylofuranosyl) uracil 11 (8 g, 17.7 mL) in an anhydrous benzene-DMSO mixture (265 mL, 6:4, v/v) were added anhydrous pyridine (1.4 mL), dicyclohexylcarbodiimide (10.9 g, 53 mmol) and dichloroacetic acid (0.75 mL). The resulting mixture was stirred at room temperature for 4 h, then diluted with ethyl acetate (400 mL) and a solution of oxalic acid (4.8 g, 53 mmol) in methanol (14 mL) was added. After being stirred for 1 h, the solution was filtered. The filtrate was washed with a saturated NaCl solution (2×500 mL), 3% $NaHCO_3$ solution (2×500 mL) and water (2×500 mL). The organic phase was dried over $Na_2SO_4$, then evaporated under reduced pressure. The resulting residue was then solubilized in an EtOH absolute-benzene mixture (140 mL, 2:1, v/v). To this solution at 0° C. was added $NaBH_4$ (0.96 g, 26.5 mmol). After being stirred for 1 h, the solution was diluted with ethyl acetate (400 mL), then filtered. The filtrate was washed with a saturated NaCl solution (400 mL) and water (400 mL). The organic phase was dried over $Na_2SO_4$, then evaporated under reduced pressure. The resulting crude material was purified by silica gel column chromatography [eluent: stepwise gradient of methanol (0–3%) in dichloromethane to give 12 (5.3 g, 66%) which was crystallized from acetontrile: mp=182–183° C.; $^1$H-NMR (DMSO-$d_6$): δ11.35 (br s, 1H, NH), 8.0–7.5 (m, 11H, 2 $C_6H_5CO$, H-6), 6.23 (br s, 1H, OH-2'), 6.15 (d, 1H, H-1', $J_{1'-2'}$=4 Hz), 5.54 (d, 1H, H-5, $J_{5-6}$=8.1 Hz), 5.37 (t, 1H, H-3', $J_{3'-2'}$=$J_{3'-4'}$=2.6 Hz), 4.7–4.6 (m, 2H, H-5' and H-5"), 4.5 (m, 1H, H-4'), 4.4 (m, 1H, H-2'); MS: FAB>0 (matrix GT) m/z 453 $(M+H)^+$, 341 $(S)^+$, 113 $(BH_2)^+$, 105 $(C_6H_5CO)^+$; FAB<0 (matrix GT) m/z 451 $(M-H)^-$, 121 $(C_6H_5CO_2)^-$, 111 $(B)^-$; Anal. Calcd for $C_{23}H_{20}N_2O_8$: C, 61.06; H, 4.46; N, 6.19. Found: C, 60.83; H, 4.34; N, 6.25.

1-(3,5-Di-O-benzoyl-2-deoxy-β-L-erythro-pentofuranosyl)uracil (13)

To a solution of 1-(3,5-di-O-benzoyl-β-L-arabinofuranosyl)uracil 12 (5.2 g, 11.4 mmoL) in anhydrous 1,2-dichloroethane (120 mL) were added phenoxythiocarbonyl chloride (4.7 mL, 34.3 mL) and 4-(dimethylamino) pyridine (DMAP, 12.5 g, 102.6 mmoL). The resulting solution was stirred at room temperature under argon atmosphere for 1 h and then evaporated under reduced pressure. The residue was dissolved in dichloromethane (300 mL) and the organic solution was successively washed with an ice-cold 0.2 N hydrochloric acid solution (3×200 mL) and water (2×200 mL), dried over $Na_2SO_4$ then evaporated under reduced pressure. The crude material was co-evaporated several times with anhydrous dioxane and dissolved in this solvent (110 mL). To the resulting solution were added under argon tris-(trimethylsilyl)silane hydride (4.2 mL, 13.7 mmol) and α,α'-azoisobutyronitrile (AIBN, 0.6 g, 3.76 mmol). The reaction mixture was heated and stirred at 100° C. for 1 h under argon, then cooled to room temperature and evaporated under reduced pressure. The residue was purified by silica gel column chromatography [eluent: stepwise gradient of methanol (0–5%)] to give 13 (2.78 g, 56%) which was crystallized from EtOH: mp=223–225° C.; $^1$H-NMR (DMSO-$d_6$): δ11.4 (br s, 1H, NH), 8.0–7.5 (m, 11H, 2 $C_6H_5CO$, H-6), 6.28 (t, 1H, H-1', J=7 Hz), 5.5 (m, 2H, H-1' and H-5), 4.6–4.4 (m, 3H, H-4', H-5' and H-5"), 2.6 (in, 2H, H-2' and H-2"); MS: FAB>0 (matrix GT) m/z 437 $(M+H)^+$, 3325 $(s)^+$, FAB<0 (matrix GT) m/z 435 $(M-H)^-$, 111 $(B)^-$; Anal. Calcd for $C_{23}H_{20}N_2O_7$: C, 63.30; H, 4.62; N, 6.42. Found: C, 62.98; H14.79; N, 6.40.

2'-Deoxy-β-L-cytidine (β-L-dC)

Lawesson's reagent (1.72 g, 4.26 mmol) was added under argon to a solution of 1-(3,5-di-O-benzoyl-2-deoxy-β-L-erythro-pentofuranosyl)uracil 13 (2.66 g, 6.1 mmol) in anhydrous 1,2-dichloroethane (120 mL) and the reaction mixture was stirred under reflux for 2 h. The solvent was then evaporated under reduced pressure and the residue was purified by silica gel column chromatography [eluent: stepwise gradient of ethyl acetate (0–8%) in dichloromethane] to give the 4-thio intermediate as a yellow foam. A solution of this thio-intermediate (1.5 g, 3.31 mmol) in methanolic ammonia (previously saturated at −10° C. and tightly stopped) (50 mL) was heated at 100° C. in a stainless-steel bomb for 3 h and then cooled to 0° C. The solution was evaporated under reduced pressure. The resulting crude material was purified by silica gel column chromatography [eluent: stepwise gradient of methanol(0–20%) in dichloromethane]. Finally, the appropriate fractions were pooled, filtered through a unit Millex HV-4 (0.45 μm, Millipore) and evaporated under reduced pressure to provide the desired 2'-deoxy-β-L-cytidine (β-L-dC) as a foam (0.6 g, 80%) which was crystallized from absolute EtOH: mp=198–199° C.; $^1$H-NMR (DMSO-$d_6$): δ7.77 (d, 1H, H-6, $J_{6\text{-}5}$=7.4 Hz), 7.10 (br d, 2H, NH-$_2$), 6.13 (t, 1H, H-1', J=6.7 Hz), 5.69 (d, 1H, H-5, $J_{5\text{-}6}$=7.4 Hz), 5.19 (d, 1H, OH-3', $J_{OH\text{-}3'}$=4.1 Hz), 4.96 (t, 1H, OH-5', $J_{OH\text{-}5'}$=$J_{OH\text{-}5''}$=5.2 Hz), 4.1 (m, 1H, H-3'), 3.75 (m, 1H, H-4'), 3.5 (m, 2H, H-5' and H-5"), 2.0 (m, 1H, H-2'), 1.9 (m, 1H, H-2"); MS: FAB>0 (matrix GT) m/z 228 $(M+H)^+$, 112 $(BH_2)^+$; FAB<0 (matrix GT) m/z 226$(M-H)^-$; $[\alpha]^{20}_D$=−69 (c 0.52, DMSO) [$[\alpha]^{20}_D$=+76 (c 0.55, DMSO) for a commercially available hydrochloride salt of the D-enantiomer]. Anal. Calcd for $C_9H_{13}N_3O_4$: C, 47.57; H, 5.77; N, 18.49. Found: C, 47.35; H, 5.68; N, 18.29.

EXAMPLE 4

Stereoselective Synthesis of 2'-Deoxy-β-L-Cytidine (β-L-dC)

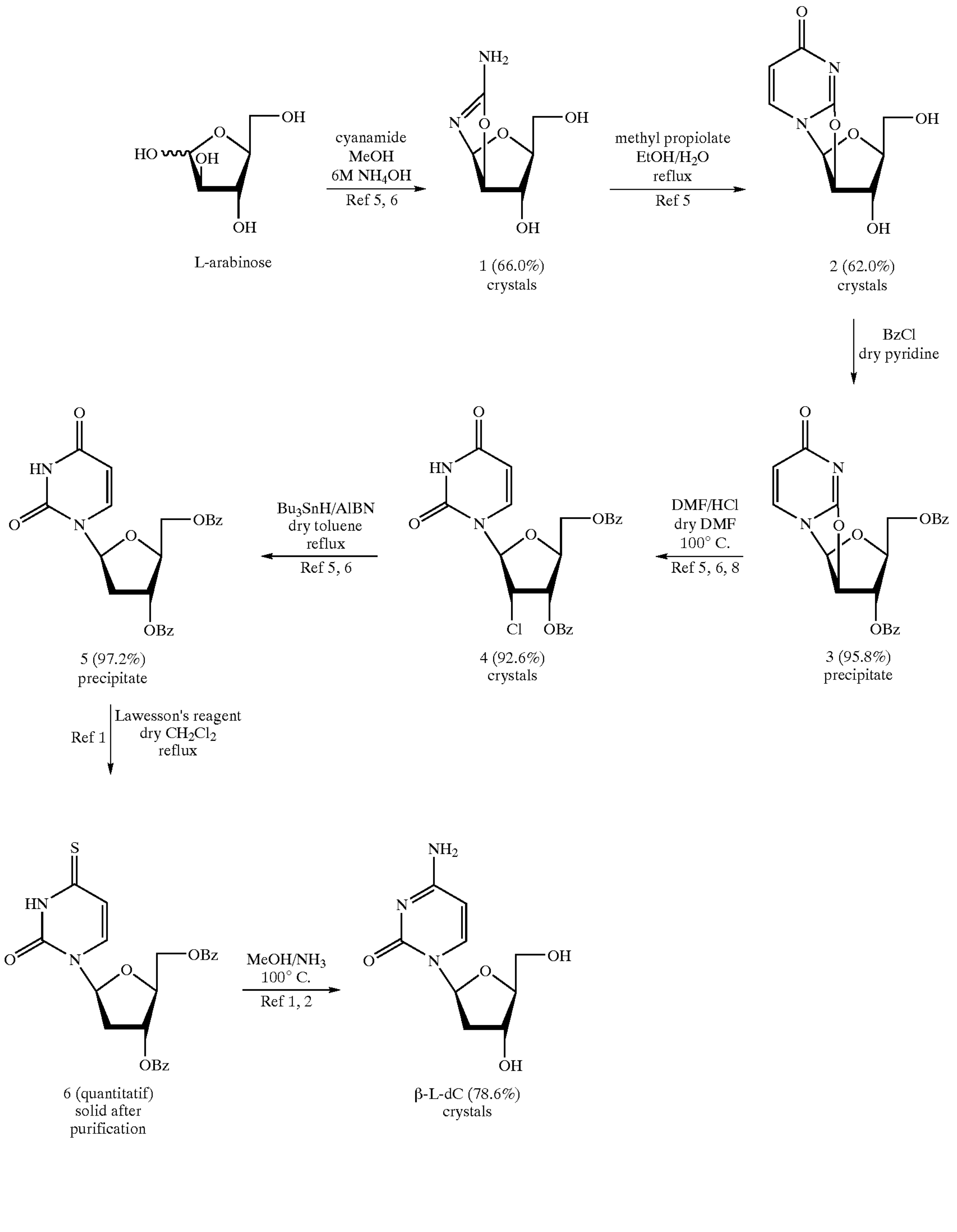

2-Amino-β-L-arabinofurano[1',2':4,5]oxazoline (1)

A mixture of L-arabinose (170 g, 1.13 mol), cyanamide (100 g, 2.38 mol), methanol (300 ml), and 6M-$NH_4OH$ (50 ml) was stirred at room temperature for 3 days and then kept at −10° C. overnight. The product was collected with suction, washed successively with methanol and ether, and dried in vacuo. Yield, 130 g (66.0%) of the analytically pure compound 1, m.p. 170–172° C.; $^1H$ NMR (DMSO-$d_6$) δ ppm 6.35 (br s, 2H, $NH_2$), 5.15 (d, 1H, H-1, J=5.6 Hz), 5.45 (br s, 1H), OH-3), 4.70 (br s, 1H, OH-5), 4.55 (d, 1H, H-2, J=5.6 Hz), 4.00 (br s, 1H, H-3), 3.65 (m, 1H, H-4), 3.25 (m, 2H, H-5, H-5').

Reagents:

L-arabinose: Fluka, >99.5%, ref 10839
Cyanamide: Fluka, >98%, ref 28330

$O^{2,2'}$-anhydro-β-L-uridine (2)

A solution of compound 1 (98.8 g, 0.57 mol) and methyl propiolate (98 ml) in 50% aqueous ethanol (740 ml) was refluxed for 5 h, then cooled and concentrated under diminished pressure to the half of the original volume. After precipitation with acetone (600 ml), the product was collected with suction, washed with ethanol and ether, and dried. The mother liquor was partialy concentrated, the concentrate precipitated with acetone (1000 ml), the solid collected with suction, and washed with acetone and ether to afford another crop of the product. Over-all yield, 80 g (62%) of compound 2, m.p. 236–240° C.; $^1H$ NMR (DMSO-$d_6$) δ ppm 7.87 (d, 1H, H-6, J=7.4 Hz), 6.35 (d, 1H, H-1', J=5.7 Hz), 5.95 (d, 1H, H-5, J=7.4 Hz), 5.90 (d, 1H, OH-3'), 5.20 (d, 1H, H-2', J=5.7 Hz), 5.00 (m, 1H, OH-3'), 4.44 (br s, 1H, H-3'), 4.05 (m, 1H, H-4'), 3.25 (m, 2H, H-5, H-5')

Reagent:

Methyl propiolate: Fluka, >97%, ref 81863

3',5'-Di-O-benzoyl-$O^{2,2'}$-anhydro-β-L-uridine (3)

To a solution of compound 2 (71.1 g, 0.31 mol) in anhydrous pyridine (1200 ml) was added benzoyl chloride (80.4 ml) at 0° C. and under argon. The reaction mixture was stirred at room temperature for 5 h under exclusion of atmospheric moisture and stopped by addition of ethanol. The solvents were evaporated under reduced pressure and the resulting residue was coevaporated with toluene and absolute ethanol. The crude mixture was then diluted with ethanol and the precipitate collected with suction, washed successively with ethanol and ether, and dried. Yield, 129 g (95.8%) of compound 3, m.p. 254° C.; $^1H$ NMR (DMSO-$d_6$) δ ppm 8.1–7.4 (m, 11H, $C_6H_5CO$, H-6), 6.50 (d, 1H, H-1', J=5.7 Hz), 5.90 (d, 1H, H-5, J=7.5 Hz), 5.80 (d, 1H, H-2', J=5.8 Hz), 5.70 (d, 1H, H-3') 4.90 (m, 1H, H-4'), 4.35 (m, 2H, H-5, H-5').

Reagent:

Benzoyl chloride: Fluka, p.a., ref 12930

3',5'-Di-O-benzoyl-2'-chloro-2'-deoxy-β,L-uridine (4)

To a solution of compound 3 (60.3 g, 0.139 mol) in dimethylformamide (460 ml) was added at 0° C. a 3.2 N-HCl/DMF solution (208 ml, prepared in situ by adding 47.2 ml of acetyl chloride at 0° C. to a solution of 27.3 ml of methanol and 133.5 ml of dimethylformamide). The reaction mixture was stirred at 100° C. for 1 h under exclusion of atmospheric moisture, cooled down, and poured into water (4000 ml). The precipitate of compound 4 was collected with suction, washed with water, and recrystallised from ethanol. The crystals were collected, washed with cold ethanol and ether, and dried under diminished pressure. Yield, 60.6 g (92.6%) of compound 4, m.p. 164–165° C.; $^1H$ NMR (DMSO-$d_6$) δ ppm 8.7 (br s, 1H, NH), 8.1–7.3 (m, 11H, $C_6H_5CO$, H-6), 6.15 (d, 1H, H-1', J=4.8 Hz), 5.5 (m, 2H, H-5, H-2'), 4.65 (m, 4H, H-3', H-4', H-5', H-5").

Reagent:

Acetyl chloride: Fluka, p.a., ref 00990

3',5'-Di-O-benzoyl-2'-deoxy-β,L-uridine (5)

A mixture of compound 4 (60.28 g, 0.128 mol), tri-n-butyltin hydride (95 ml) and azabisisobutyronitrile (0.568 g) in dry toluene (720 ml) was refluxed under stirring for 5 h and cooled down. The solid was collected with suction and washed with cold toluene and petroleum ether. The filtrate was concentrated under reduced pressure and diluted with petroleum ether to deposit an additional crop of compound 5. Yield, 54.28 g (97.2%) of compound 5; m.p. 220–221° C.; $^1H$ NMR ($CDCl_3$) δ ppm 8.91 (br s, 1H, NH), 8.1–7.5 (m, 11H, $C_6H_5CO$ and H-6), 6.43 (q, 1H, H-1', $J_{1',2'}$=57 Hz and $J_{1',2''}$=8.3 Hz), 5.7–5.6 (m, 2H, H-3' and H-5), 4.8–4.6 (m, 3H, H-5', H-5" and H-4'), 2.8–2.7 (m, 1H, H-2'), 2.4–2.3 (m, 1H, H-2").

Reagents:

Tri-n-butyltin hydride: Fluka, >98%, ref 90915
Azabisisobutyronitrile: Fluka, >98%, ref 11630

3',5'-Di-O-benzoyl-2'-deoxy-β-L-4-thio-uridine (6)

A solution of compound 5 (69 g, 0.158 mol) and Lawesson's reagent (74 g) in anhydrous methylene chloride (3900 ml) was refluxed under argon overnight. After evaporation of the solvant, the crude residue was purified by a silica gel column chromatography [eluant: gradient of methanol (0–2%) in methylene chloride] to afford pure compound 6 (73 g) in quantitative yield; $^1H$ NMR ($CDCl_3$) δ ppm 9.5 (br s, 1H, NH), 8.1–7.4 (m, 10H, $C_6H_5CO$), 7.32 (d, 1H, H-6, J=7.7 Hz), 6.30 (dd, 1H, H-1', J=5.6 Hz and J=8.2 Hz), 6.22 (d, 1H, H-5, J=7.7 Hz), 5.6 (m, 1H, H-3'), 4.7 (m, 2H, H-5', H-5"), 4.5 (m, 1H, H-4'), 2.8 (m, 1H, H-2'), 2.3 (m, 1H, H-2").

Reagent:

Lawesson's reagent: Fluka, >98%, ref 61750

2'-Deoxy-β-L-cytosine

A solution of compound 6 (7.3 g, 0.016 mol) in methanol saturated with ammonia (73 ml) was heated at 100° C. in a stainless steel cylinder for 3 h. After cooling carefully, the solvent was evaporated under reduced pressure. An aqueous solution of the residue was washed with ethyl acetate and evaporated to dryness. Such a procedure was carried out on 9 other samples (each 7.3 g) of compound 6 (total amount of 6=73 g). The 10 residues were combined, diluted with absolute ethanol and cooled to give 7 as crystals. Trace of benzamide were eliminated from the crystals of 6 by a solid-liquid extraction procedure (at reflux in ethyl acetate for 1 h). Yield, 28.75 g (78.6%) of compound 6; m.p. 141–145° C.; $^1H$ NMR (DMSO) δ ppm 8.22 and 8.00 (2 br s, 2H, $NH_2$), 7.98 (d, 1H, H-6, J=7.59 Hz), 6.12 (t, 1H, H-1', J=6.5 Hz and J=7.6 Hz), 5.89 (d, 1H, H-5, J=7.59 Hz), 5.3 (br s, 1H, OH-3'), 5.1 (br s, 1H, OH-5'), 4.2 (m, 1H, H-3'), 3.80 (q, 1H, H-4', J=3.6 Hz and J=6.9 Hz), 3.6–3.5 (m, 2H, H-5', H-5"), 2.2–2.0 (m, 2H, H-2', H-2"); FAB<0, (GT) m/e 226 $(M-H)^-$, 110 $(B)^-$; FAB>0 (GT) 228 $(M+H)^+$, 112 $(B+2H)^+$; $[\alpha]_D^{20}$−56.48 (c=1.08 in DMSO); UV (pH 7) $\lambda_{max}$=270 nm (ε=10000).

Reagent:

Methanolic ammonia: previously saturated at −5° C., tightly stoppered, and kept in a freezer.

EXAMPLE 5

Stereoselective Synthesis of 2'-Deoxy-β-L-Thymidine (β-L-dT)

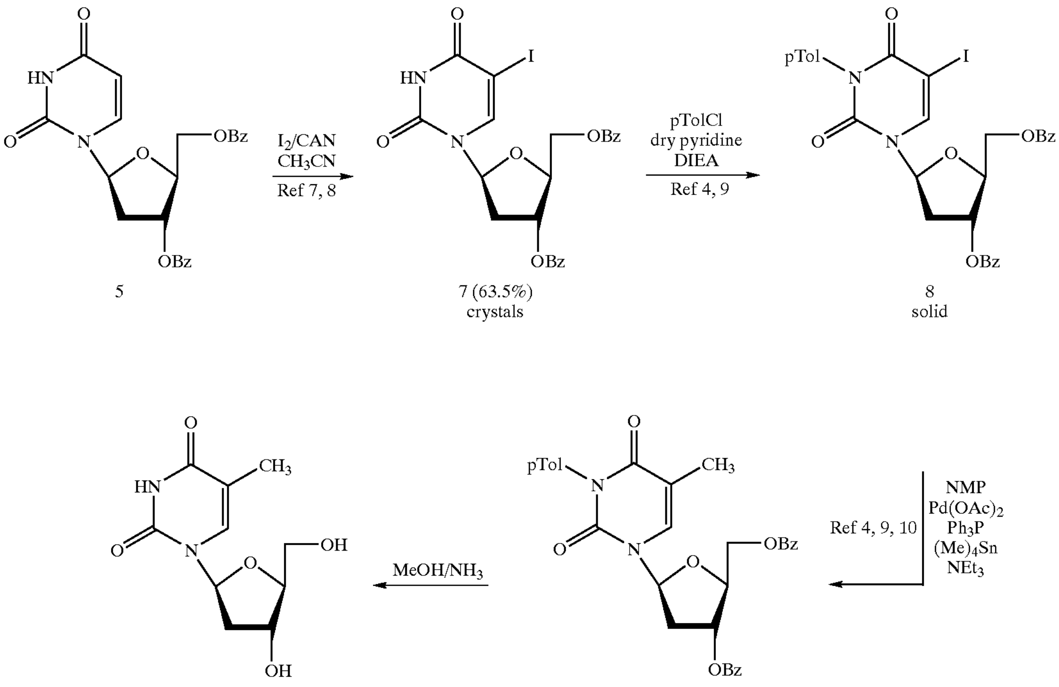

5
7 (63.5%) crystals
8 solid
β-L-dT (64.8%) crystals after purification
9 (48.3%, 2 steps) solid after purification 3',5'-Di-O-benzoyl-2'-deoxy-5-iodo-β-L-uridine (7)

A mixture of compound 5 (105.8 g, 0.242 mol), iodine (76.8 g), CAN (66.4 g) and acetonitrile (2550 ml) was stirred at 80° C. for 3 h then the reaction mixture was cooled at room temperature leading to crystallization of compond 7 (86.6 g, 63.5%); m.p. 192–194° C.; $^1$H NMR (DMSO) δ ppm 0.8.34 (s, 1H, NH), 8.2–7.2 (m, 11H,2 $C_6H_5CO$, H-6), 6.31 (q, 1H, H-1', J=5.5 Hz and J=8.7 Hz), 5.5 (m, 1H, H-3'), 4.7 (m, 2H, H-5', H-5"), 4.5 (m, 1H, H-4'), 2.7 (m, 1H, H-2'), 2.3 (m, 1H, H-2"); FAB<0, (GT) m/e 561 $(M-H)^-$, 237 $(B)^-$; FAB>0 (GT) 563 $(M+H)^+$; $[\alpha]_D^{20}$+39.05 (c=1.05 in DMSO); UV (EtOH 95) $\upsilon_{max}$=281 nm (ε=9000), $\upsilon_{min}$=254 nm (ε=4000), $\upsilon_{max}$=229 nm (ε=31000); Anal. Calcd for $C_{23}H_{19}IN_2O_7$: C, 49.13; H, 3.41; N, 4.98; I, 22.57. Found: C, 49.31; H, 3.53; N, 5.05; I, 22.36.

Reagents:

Iodine: Fluka, 99.8%, ref 57650

Cerium ammonium nitrate (CAN): Aldrich, >98.5%, ref 21,547-3

3',5'-Di-O-benzoyl-2'-deoxy-3-N-toluoyl-β-L-thymidine (9)

To a solution of compound 7 (86.6 g, 0.154 mol) in anhydrous pyridine (1530 ml) containing N-ethyldiisopropylamine (53.6 ml) was added, portionwise at 0° C., p-toluoyl chloride (40.6 ml). The reaction mixture was stirred for 2 h at room temperature, then water was added to stop the reaction and the reaction mixture was extracted with methylene chloride. The organic phase was washed with water, dried over sodium sulfate and evaporated to dryness to give crude 3',5'-di-O-benzoyl-2'-deoxy-3-N toluoyl-5-iodo-β-L-uridine (8) which can be used for the next step without further purification.

A solution of the crude mixture 8, palladium acetate (3.44 g), triphenylphosphine (8.0 g) in N-methylpyrolidinone (1375 ml) with triethylamine (4.3 ml) was stirred at room temperature for 45 min. Then, tetramethyltin (42.4 ml) was added dropwise at 0C under argon. After stirring at 100–110° C. overnight, the reaction mixture was poured into water and extracted with diethyl ether. The organic solution was dried over sodium sulfate and concentrated under reduced pressure. The residue was purified by a silica gel column chromatography [eluant: stepwise gradient of ethyl acetate (0–10%) in toluene] to give compound 9 as a foam (42.3 g, 48.3% for the 2 steps). $^1$H NMR (DMSO) δ ppm 0.8.3–7.2 (m, 15H,2 $C_6H_5CO$, 1 $CH_3C_6H_4CO$, H-6), 6.29 (t, 1H, H-1', J=7.0 Hz), 5.7 (m, 1H, H-3'), 4.7–4.5 (m, 3H, H-5', H5", H-4'), 2.7–2.6 (m, 2H, H-2', H-2"); FAB<0, (GT) m/e 567 $(M-H)^-$, 449 $(M-CH_3C_6H_4CO)^-$, 243 $(B)^-$, 121 $(C_6H_5COO)^-$; FAB>0 (GT) 1137 $(2M+H)^+$, 569 $(M+H)^+$, 325 $(M-B)^-$, 245 $(B+2H)^+$, 119 $(CH_3C_6H_5CO)^-$;

Reagents:

p-Toluoyl chloride, Aldrich, 98%, ref 10,663-1

Diisopropylethylamine: Aldrich, >99.5%, ref 38,764-9

N-methylpyrolidinone: Aldrich, >99%, ref 44,377-8

Paladium acetate: Aldrich, >99.98%, ref 37,987-5

Triphenylphosphine: Fluka, >97%, ref 93092

Tetramethyltin: Aldrich, >99%, ref 14,647-1

2'-Deoxy-β-L-thymidine

A solution of compound 9 (42.3 g, 0.074 mol) in methanol saturated with ammonia (1850 ml) was stirred at room temperature for two days. After evaporation of the solvent, the residue was diluted with water and washed several times with ethyl acetate. The aqueous layer was separated, evaporated under reduced pressure and the residue was purified by a silica gel column chromatography [eluant: stepwise gradient of methanol (0–10%) in methylene chloride] to give pure 2'-deoxy-β-L-thymidine (11.62 g, 64.8%) which was crystallized from ethanol; m.p. 185–188° C.; $^1$H NMR (DMSO) δ ppm 11.3 (s, 1H, NH), 7.70 (s, 1H, H-6), 6.2 (pt, 1H, H-1'), 5.24 (d, 1H, OH-3', J=4.2 Hz), 5.08 (t, 1H, OH-5', J=5.1 Hz), 4.2 (m, 1H, H-3'), 3.7 (m, 1H, H-4'), 3.5–3.6 (m, 2H, H-5', H-5"), 2.1–2.0 (m, 2H, H-2', H-2"); FAB<0, (GT) m/e 483 $(2M-H)^-$, 349 $(M+T-H)^-$; 241 $(M-H)^-$, 125 $(B)^-$; FAB>0 (GT) 243 $(M+H)^+$, 127 $(B+2H)^+$; $)^+$; $[\alpha]_D^{20}-13.0$ (c=1.0 in DMSO); UV (pH 1) $\upsilon_{max}$=267 nm (ε=9700), $\upsilon_{min}$=234 nm (ε=2000).

Reagent:

Methanolic ammonia: previously saturated at −5° C., tightly stoppered, and kept in a freezer.

EXAMPLE 6

Stereoselective Synthesis of 2'-deoxy-β-L-inosine (β-L-dI)

β-L-dI was synthesized by deamination of 2'-deoxy-β-L-adenosine (β-L-dA) following a procedure previously described in the 9-D-glucopyranosyl series (Ref: I. Iwai, T. Nishimura and B. Shimizu, Synthetic Procedures in Nucleic Acid Chemistry, W. W. Aorbach and R. S. Tipson, eds., John Wiley & Sons, Inc. New York, vol. 1, pp. 135–138 (1968)).

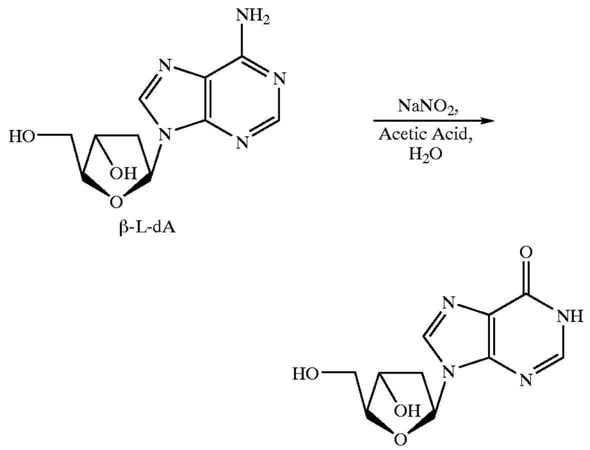

β-L-dA

β-L-dI

Thus, a solution of β-L-dA (200 mg) in a mixture of acetic acid (0.61 ml) and water (19 ml) was heated with sodium nitrite (495 mg), and the mixture was stirred at room temperature overnight. The solution was then evaporated to dryness under diminished pressure. An aqueous solution of the residue was applied to a column of IR-120 $(H^+)$ ion-exchange resin, and the column was eluted with water. Appropriate fractions were collected and evaporated to dryness to afford pure β-L-dI which was crystallized from methanol (106 mg, 53% yield not optimized): m.p.=209°–211° C.; UV $(H_2O)$, $\lambda_{max}$=247 nm; $^1$H-NMR (DMSO-$d_6$)=8.32 and 8.07 (2s, 1H each, H-2 and H-8), 6.32 (pt, 1H, H-1; J=6.7 Hz), 4.4 (m, 1H, H-3'), 3.9 (m, 1H, H-4'), 3.7–3.4 (m, 2H partially obscured by HOD, H-5',5"), 2.6 and 2.3 (2m, 1H each, H-2' and H-2"); mass spectra (mature, glycerol-thioglycerol, 1:1, v/v), FAB>0: 253 $(m+H)^+$, 137 $(base+2H)^+$; FAB<0: 251 $(m-H)^-$, 135 $(base)^-$; $[\alpha]_D^{20}$=+19.3 (−c 0.88, $H_2O$).

Anti-HBV Activity of the Active Compounds

The ability of the active compounds to inhibit the growth of virus in 2.2.15 cell cultures (HepG2 cells transformed with hepatitis virion) can be evaluated as described in detail below.

A summary and description of the assay for antiviral effects in this culture system and the analysis of HBV DNA has been described (Korba and Milman, 1991, *Antiviral Res.,* 15:217). The antiviral evaluations are performed on two separate passages of cells. All wells, in all plates, are seeded at the same density and at the same time.

Due to the inherent variations in the levels of both intracellular and extracellular HBV DNA, only depressions greater than 3.5-fold (for HBV virion DNA) or 3.0-fold (for HBV DNA replication intermediates) from the average levels for these HBV DNA forms in untreated cells are considered to be statistically significant (P<0.05). The levels of integrated HBV DNA in each cellular DNA preparation (which remain constant on a per cell basis in these experiments) are used to calculate the levels of intracellular HBV DNA forms, thereby ensuring that equal amounts of cellular DNA are compared between separate samples.

Typical values for extracellular HBV virion DNA in untreated cells range from 50 to 150 pg/ml culture medium (average of approximately 76 pg/ml). Intracellular HBV DNA replication intermediates in untreated cells range from 50 to 100 μg/pg cell DNA (average approximately 74 pg/μg cell DNA). In general, depressions in the levels of intracellular HBV DNA due to treatment with antiviral compounds are less pronounced, and occur more slowly, than depressions in the levels of HBV virion DNA (Korba and Milman, 1991, Antiviral Res., 15:217).

The manner in which the hybridization analyses are performed for these experiments result in an equivalence of approximately 1.0 pg of intracellular HBV DNA to 2–3 genomic copies per cell and 1.0 pg/ml of extracellular HBV DNA to $3\times10^5$ viral particles/ml.

EXAMPLE 7

The ability of the triphosphate derivatives of β-L-dA, β-L-dC, β-L-dU, β-L-2'-dG, β-L-dI, and β-L-dT to inhibit hepatitis B was tested. Table 1 describes the comparative inhibitory activities of triphosphates of β-L-dT (β-L-dT-TP), β-L-dC (β-L-dC-TP), β-L-dU (β-L-dU-TP) and β-L-dA (β-L-dA-TP) on woodchuck hepatitis virus (WHV) DNA polymerase, human DNA polymerases α, β, and γ.

TABLE 1

| Inhibitor | WHV DNA pol $IC_{50}$ | DNA pol α $K_i^b$ (μM) | DNA pol β $K_i^b$ (μM) | DNA pol γ $K_i^b$ (μM) |
|---|---|---|---|---|
| β-L-dT-TP | 0.34 | >100 | >100 | >100 |
| β-L-dA-TP | 2.3 | >100 | >100 | >100 |
| β-L-dC-TP | 2.0 | >100 | >100 | >100 |
| β-L-dU-TP | 8 | >100 | >100 | >100 |

[a]$IC_{50}$: 50% Inhibitory concentration

[b]$K_i$ value was determined using calf thymus activated DNA as template-primer and dATP as substrate. Inhibitors were analyzed by Dixon plot analysis. Under these conditions, the calculated mean $K_m$ of human DNA polymerase α for dATP as approximately 2.6 μM. Human DNA polymerase β exhibited a steady state $K_m$ of 3.33 μM for dATP. Human DNA polymerase γ exhibited a steady $K_m$ of 5.2 μM.

EXAMPLE 8

The anti-hepatitis B virus activity of β-L-dA, β-L-dC, β-L-dU, β-L-2'-dG and β-L-dT was tested in transfected Hep G-2 (2.2.15) cells. Table 2 illustrates the effect of β-L-dA, β-L-dC, β-L-dU, and β-L-dT against hepatitis B virus replication in transfected Hep G-2 (2.2.15) cells.

TABLE 2

| Compound | HBV virions[a] $EC_{50}$ ($\mu$M) | HBV Ri[b] $EC_{50}$ ($\mu$M) | Cytotoxicity $IC_{50}$ ($\mu$M) | Selectivity Index $IC_{50}/EC_{50}$ |
|---|---|---|---|---|
| β-L-dT | 0.05 | 0.05 | >200 | >4000 |
| β-L-dC | 0.05 | 0.05 | >200 | >4000 |
| β-L-dA | 0.10 | 0.10 | >200 | >2000 |
| β-L-dI | 1.0 | 1.0 | >200 | >200 |
| β-L-dU | 5.0 | 5.0 | >200 | >40 |

[a]Extracellular DNA
[b]Replicative intermediates (Intracellular DNA)

EXAMPLE 9

The effect of β-L-dA, β-L-dC and β-L-dT in combination on the growth of hepatitis B was measured in 2.2.15 cells. The results are provided in Table 3.

TABLE 3

| Combination | Ratio | $EC_{50}$ |
|---|---|---|
| L-dC + L-dT | 1:3 | .023 |
| L-dC + L-dT | 1:1 | .053 |
| L-dC + L-dT | 3:1 | .039 |
| L-dC + L-dA | 1:30 | .022 |
| L-dC + L-dA | 1:10 | .041 |
| L-dC + L-dA | 1:3 | .075 |
| L-dT + L-dA | 1:30 | .054 |
| L-dT + L-dA | 1:10 | .077 |
| L-dT + L-dA | 1:3 | .035 |

Each combination produced anti-HBV activity that was synergistic. In addition, the combination of L-dA+L-dC+L-dT was also synergistic in this model.

EXAMPLE 10

The inhibition of hepatitis B replication in 2.2.15 cells by β-L-DA and β-L-dC, alone and in combination was measured. The results are shown in Table 4.

TABLE 4

| [a]β-L-2'-deoxy-adenosine ($\mu$M) | [b]β-L-2'-deoxy-cytidine ($\mu$M) | % Inhibition | [c]C.I. |
|---|---|---|---|
| 0.5 | | 90 | |
| 0.05 | | 24 | |
| 0.005 | | 1 | |
| | 0.5 | 95 | |
| | 0.05 | 40 | |
| | 0.005 | 10 | |
| 0.05 | 0.05 | 80 | 0.34 |
| 0.05 | 0.005 | 56 | 0.20 |
| 0.05 | 0.0005 | 50 | 0.56 |
| 0.005 | 0.05 | 72 | 0.35 |
| 0.005 | 0.005 | 54 | 0.35 |
| 0.005 | 0.0005 | 30 | 0.16 |
| 0.0005 | 0.05 | 50 | 0.83 |
| 0.0005 | 0.005 | 15 | 0.28 |
| 0.0005 | 0.0005 | 0 | N.A. |

[a]β-L-2'-deoxy-adenosine: $IC_{50}$ = 0.09 $\mu$M
[b]β-L-2'-deoxy-cytidine: $IC_{50}$ = 0.06 $\mu$M
[c]Combination indices values indicate synergism effect (<1), additive effect (=1), and antagonism effect (>1)

EXAMPLE 11

The efficacy of L-dA, L-dT and L-dC against hepadnavirus infection in woodchucks (*Marmota monax*) chronically infected with woodchuck hepatitis virus (WHV) was determined. This animal model of HBV infection is widely accepted and has proven to be useful for the evaluation of antiviral agents directed against HBV.

Protocol:

Experimental groups (n=3 animals/drug group, n=4 animals/control)

| | |
|---|---|
| Group 1 | vehicle control |
| Group 2 | lamivudine (3TC) (10 mg/kg/day) |
| Groups 3–6 | L-dA (0.01, 0.1, 1.0, 10 mg/kg/day) |
| Groups 7–10 | L-dT (0.01, 0.1, 1.0, 10 mg/kg/day) |
| Groups 11–14 | L-dC (0.01, 0.1, 1.0, 10 mg/kg/day) |

Drugs were administered by oral gavage once daily, and blood samples taken on days 0, 1, 3, 7, 14, 21, 28, and on post-treatment days +1, +3, +7, +14, +28 and +56. Assessment of the activity and toxicity was based on the reduction of WHV DNA in serum: dot-blot, quantative PCR.

Figure 3:
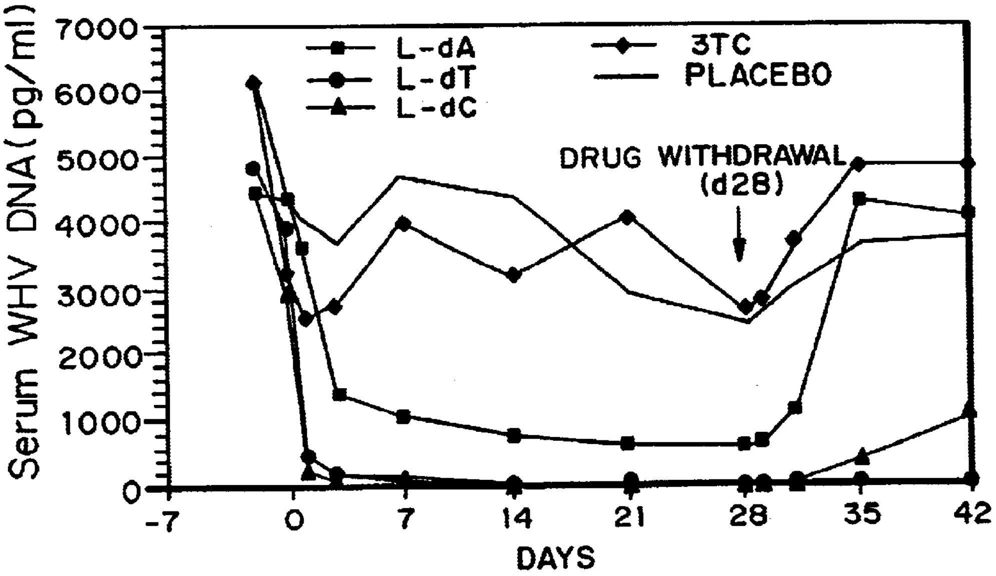
FIG. 3 is a graph which illustrates the antiviral effect of β-L-dA, β-L-dT and β-L-dC in the woodchuck chronic hepatitis model.

The results are illustrated in FIG. 3 and Table 5.

TABLE 5

Antiviral Activity of LdA, LdT, LdC in Woodchuck Model of Chronic HBV Infection

| day | Control | LdA | LdT | LdC |
|---|---|---|---|---|
| | ng WHV-DNA per ml serum[1,2] | | | |
| 0 | 381 | 436 | 423 | 426 |
| 1 | 398 | 369 | 45 | 123 |
| 3 | 412 | 140 | 14 | 62 |
| 7 | 446 | 102 | 6 | 46 |
| 14 | 392 | 74 | 1 | 20 |

[1]LdA, LdT, LdC administered orally once a day at 10 mg/kg
[2]limit of detection is 1 ng/ml WHV-DNA per ml serum The data show that L-dA, L-dT and L-dC are highly active in this in vivo model. First, viral load is reduced to undetectable (L-dT) or nearly undetectable (L-dA, L-dC) levels. Second, L-dA, L-dT and L-dC are shown to be more active than 3TC (lamivudine) in this model. Third, viral rebound is not detected for at least two weeks after withdrawal of L-dT. Fourth, dose response curves suggest that a modes increase in the dose of L-dA and L-dC would show antiviral activity similar to L-dT. Fifth, all animals receiving the drugs gained weight and no drug-related toxicity was detected.

EXAMPLE 12

Chemical Synthesis of β-L-dC 5'-L-Valyl Ester

As an illustrative example of the synthesis of β-L-dC amino esters, β-L-dC 5'-L-valyl ester is synthesized by first protecting the amine group of β-L-dC using $(CH_3)_3SiCl$. The protected β-L-dC undergoes esterification by the addition of N-Boc L-valine. The ester is then deprotected to yeild β-L-dC 5'-L-valyl ester. Other methods for synthesizing amino acid esters are disclosed in U.S. Pat. Nos. 5,700,936 and 4,957,924, incorporated herein by reference. The L-valinyl 5'-O-ester of L-dA, L-dC, L-dT, and L-dU are preferred embodiments of this invention.

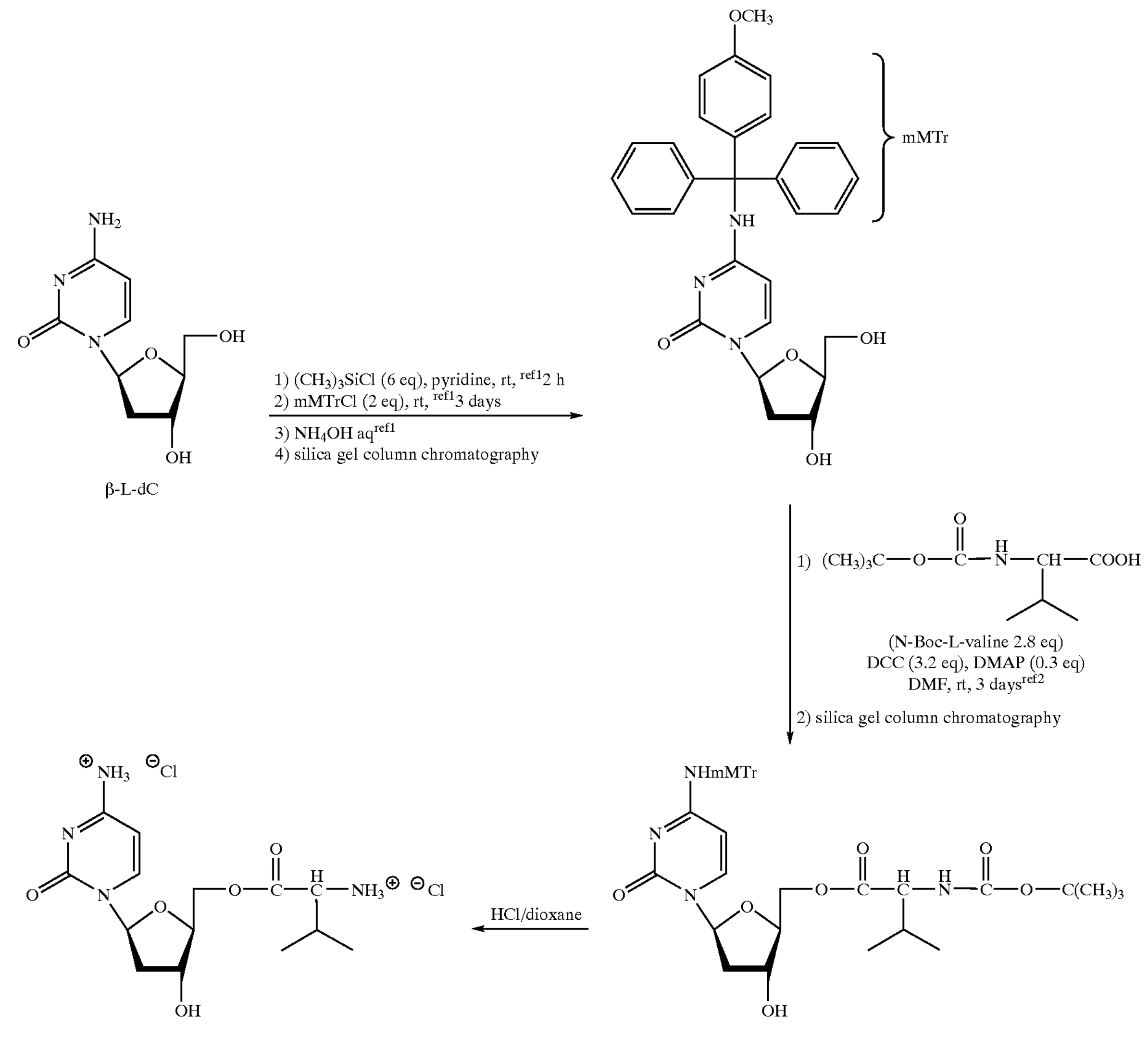

β-L-dC

β-L-dC5′-L-valyl ester

Ref 1: by modification of a previously described procedure in the D series: Nyilas, A. et al. *Tetrahedron* 46 (6), 2149–2164 (1990)

Ref 2: by modification of a previously described procedure for the acyclovir L-valyl ester: Beauchamp, L. M.. et al. *Antiviral Chemistry & Chemotherapy* 3 (3), 157–164 (1992).

Toxicity of Compounds

Toxicity analyses were performed to assess whether any observed antiviral effects are due to a general effect on cell viability. The method used is the measurement of the effect of β-L-dA, β-L-dC and β-L-dT on cell growth in human bone marrow clorogenic assays, as compared to Lamuvidine. The results are provided in Table 6.

TABLE 6

| Compound | CFU-GM (μM) | BFU-E (μM) |
|---|---|---|
| β-L-dA | >10 | >10 |
| β-L-dC | >10 | >10 |
| β-L-dT | >10 | >10 |
| β-L-dU | >10 | >10 |
| Lamuvidine | >10 | >10 |

Preparation of Pharmaceutical Compositions

Humans suffering from any of the disorders described herein, including hepatitis B, can be treated by administering to the patient an effective amount of a β-2'-deoxy-β-L-erythro-pentofuranonucleoside, for example, β-L-2'-deoxyadenosine, β-L-2'-deoxycytidine, β-L-2'-deoxyuridine, β-L-2'-deoxyguanosine or β-L-2'-deoxythymidine or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount of compound to inhibit viral replication in vivo, without causing serious toxic effects in the patient treated. By "inhibitory amount" is meant an amount of active ingredient sufficient to exert an inhibitory effect as measured by, for example, an assay such as the ones described herein.

A preferred dose of the compound for all of the above-mentioned conditions will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable prodrug can be calculated based on the weight of the parent nucleoside to be delivered. If the prodrug exhibits activity in itself, the effective dosage can be estimated as above using the weight of the prodrug, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable derivative or salts thereof can also be mixed with other active materials that do not impair the desired action, or with materials that supplement the desired action, such as antibiotics, antifungals, antiinflammatories, protease inhibitors, or other nucleoside or nonnucleoside antiviral agents. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,81 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the foregoing detailed description of the invention. It is intended that all of these variations and modifications be included within the scope of the this invention.

We claim:

1. A method for treating a human infected with hepatitis B virus comprising administering an effective amount of the β-L-nucleoside:

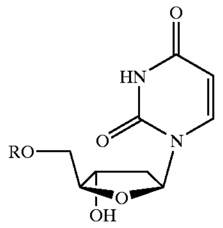

or a pharmaceutically acceptable salt thereof, wherein R is selected from the group consisting of H, mono, di or tri phosphate, an amino acid acyl residue, acyl, alkyl, and a stabilized phosphate prodrug.

2. The method according to claim 1, wherein the compound is

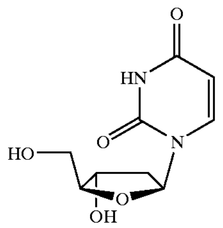

or a phannaceutically acceptable salt thereof.

3. The method of claim 1, wherein the R is a monophosphate.

4. The method of claim 1, wherein the R is a diphosphate.

5. The method of claim 1, wherein the R is a triphosphate.

6. The method of claim 1, wherein the R is an amino acid acyl residue.

7. The method of claim 1, wherein the R is acyl.

8. The method of claim 1, wherein the R is alkyl.

9. The method of claim 1, wherein the R is a stabilized phosphate prodrug.

10. The method according to claim 1, wherein the compound is administered in a pharmaceutically acceptable carrier.

11. The method according to claim 1, wherein the pharmaceutically acceptable carrier is suitable for oral delivery.

12. The method according to claim 1, wherein the pharmaceutically acceptable carrier is suitable for intravenous delivery.

13. The method according to claim 1, wherein the pharmaceutically acceptable carrier is suitable for parenteral delivery.

14. The method according to claim 1, wherein the pharmaceutically acceptable carrier is suitable for intradermal delivery.

15. The method according to claim 1, wherein the pharmaceutically acceptable carrier is suitabie for subcutaneous delivery.

16. The method according to claim 1, wherein the pharmaceutically acceptable carrier is suitable for topical delivery.

17. The method according to claim 1, wherein the compound is in the form of a dosage unit.

18. The method according to claim 17, wherein the dosage unit contains 10 to 1500 mg of the compound.

19. The method according to claim 17 or 18, wherein the dosage unit is a tablet or capsule.

20. A method for treating a human infected with hepatitis B virus comprising administering an effective amount of the β-L-nucleoside:

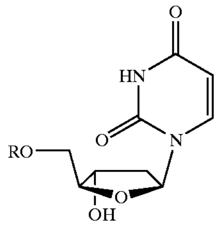

or a pharmaceutically acceptable salt or thereof, in alternation or combination with one or more other anti-hepatitis agents, wherein R is selected from the group consisting of H, mono, di or tri phosphate, an amino acid acyl residue, acyl, ailcyl, and a stabilized phosphate prodrug.

21. The method according to claim 20, wherein the anti-hepatitis agent is selected from the group consisting of β-L-2-hydroxymethyl-5-(cytosin-1-yl)-1,3-oxathiolane (3TC), cis-2-hydroxymethyl-5-(5-fluorocytosin-1-yl)-1,3-oxatbiolane (FTC), βL-2"-fluoro-5-methyl-arabinofuranosyluridine (L-FMAU), β-D-2,6-diaminopurine dioxolane (DAPD), famciclovir, penciclovir, 2-amino-1,9-dihydro-9-[4-hydroxy-3-(hydroxymethyl)-2-methylenecyclo-pentyl]-6H-purin-6-one (entecavir, BMS-200475), 9-[2-(phosphono-methoxy)ethyl]-adenine (PMEA, adefovir, dipivoxil); 9-((1R,2R,3S)-2,3-bis (hydroxyinethyl)cyclo-butyl)guanine (lobucavir), ganciclovir, and ribavirin.

22. The method according to claim 20, wherein the anti-hepatitis agent is β-L-2-hydroxymethyl-5-(cytosin-1-yl)-1,3-oxathiolane (3TC).

23. The method according to claim 20, wherein the anti-hepatitis agent is cis-2-hydroxymcthyl-5-(5-fluorocytosin-1-yl)-1,3-oxatbiolane (FTC).

24. The method according to claim 20, wherein the anti-hepatitis agent is L-2'-fluoro-5-methyl-arabinofuranosyluridine (L-FMAU).

25. The method according to claim 20, wherein the anti-hepatitis agent is β-D-2,6-diaminopurine dioxolane (DAPD).

26. The method according to claim 20, wherein the anti-hepatitis agent is famicilovir.

27. The method according to claim 20, wherein the anti-hepatitis agent is penciclovir.

28. The method according to claim 20, wherein the anti-hepatitis agent is 2-amino-1,9-dihydro-9-[4-hydroxy-3-(hydroxymethyl)-2-methylenecyclo-pentyl]-6H-purin-6-one (entecavir, BMS-200475).

29. The method according to claim 20, wherein the anti-hepatitis agent is 9-[2-(phosphono-methoxy)ethyl]-adenine (PMEA, adefovir, dipivoxil).

30. The method according to claim 20, wherein the anti-hepatitis agent is 9-((1R,2R,3S)-2,3-bis (hydroxymethyl)cyclo-butyl)guanine (lobucavir).

31. The method according to claim 20, wherein the anti-hepatitis agent is ganciclovir.

32. The method according to claim 20, wherein the anti-hepatitis agent is ribavirin.

33. The method according to claim 20, wherein the compound is administered in a pharmaceutically acceptable carrier.

34. The method according to claim 20, wherein the pharmaceutically acceptable carrier is suitable for oral delivery.

35. The method according to claim 20, wherein the pharmaceutically acceptable carrier is suitable for intravenous delivery.

36. The method according to claim 20, wherein the pharmaceutically acceptable carrier is suitable for parentcral delivery.

37. The method according to claim 20, wherein the pharmaceutically acceptable carrier is suitable for intradermal delivery.

38. The method according to claim 20, wherein the pharmaceutically acceptable carrier is suitable for subcutaneous delivery.

39. The method according to claim 20, wherein the pharmaceutically acceptable carrier is suitable for topical delivery.

40. The method according to claim 20, wherein the compound is in the form of a dosage unit.

41. The method according to claim 40, wherein the dosage unit contains 10 to 1500 mg of the compound.

42. The method according to claim 40 and 41, wherein the dosage unit is a tablet or capsule.

43. A pharmaceutical composition for treating a human infected with hepatitis B virus comprising an effective amount of the B-L-nucleoside:

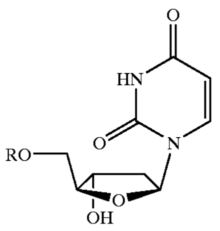

or a pharmaceutically acceptable salt or thereof, wherein R is selected from the group consisting of H, mono, di or tri phosphate, an amino acid acyl residue, acyl, alkyl, and a stabilized phosphate prodrug;

with one or more other anti-hepatitis agents; optionally in a pharmaceutically acceptable carrier.

44. The pharmaceutical composition of claim 43, wherein the β-L-nucleoside is

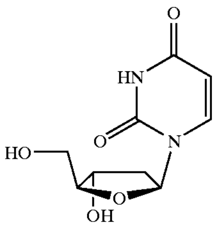

or a pharmaceutically acceptable salt thereof.

45. The pharmaceutical composition according claim 43, wherein the compound is the form of a dosage unit.

46. The pharmaceutical composition according to claim 45, wherein the dosage unit contains 10 to 1500 mg of the compound.

47. The pharmaceutical composition according claim 43, wherein the composition is administered in a pharmaceutically acceptable carrier.

48. The pharmaceutical composition according claim 43, wherein the pharmaceutically acceptable carrier is suitable for oral delivery.

49. The pharmaceutical composition according claim 43, wherein the pharmaceutically acceptable carrier is suitable for intravenous delivery.

50. The pharmaceutical composition according claim 43, wherein the pharmaceutically acceptable carrier is suitable for parenteral delivery.

51. The pharmaceutical composition according claim 43, wherein the pharmaceutically acceptable carrier is suitable for intradermal delivery.

52. The pharmaceutical composition according claim 43, wherein the pharmaceutically acceptable carrier is suitable for subcutaneous delivery.

53. The pharmaceutical composition according claim 43, wherein the pharmaceutically acceptable carder is suitable for topical delivery.

54. The method according to claim 20, wherein the R is a monophosphate.

55. The method according to claim 20, wherein the R is a diphospbate.

56. The method according to claim 20, wherein the R is a triphosphate.

57. The method according to claim 20, wherein the R is an amino acid acyl residue.

58. The method according to claim 20, wherein the R is acyl.

59. The method according to claim 20, wherein the R is alkyl.

60. The method according to claim 20, wherein the R is a stabilized phosphate prodrug.

61. The pharmaceutical composition according to claim 43, wherein the R is a monophosphate.

62. The pharmaceutical composition according to claim 43, wherein the R is a diphosphate.

63. The pharmaceutical composition according to claim 43, wherein the R is a triphosphate.

64. The pharmaceutical composition according to claim 43, wherein the R is an amino acid acyl residue.

65. The pharmaceutical composition according to claim 43, wherein the R is acyl.

66. The pharmaceutical composition according to ciaim 43, wherein the R is alkyl.

67. The pharmaceutical composition according to claim 43, wherein the R is a stabilized phosphate prodrug.

68. The pharmaceutical composition according to claim 45 or 46, wherein the dosage unit is a tablet or capsule.

69. The pharmaceutical composition according to claim 43, wherein the anti-hepatitis agent is selected from the group consisting of β-L-2-hydroxymcthyl-5-(cytosin-1-yl)-1,3-oxathiolane (3TC), cis-2-hydroxymethyl-5-(5-fluorocytosin-1-yl)-1,3-oxathiolane (FTC), β-L-2'-fluoro-5-methyl-arabinofuranosyluridine (L-FMAU), β-D-2,6-diaminopurine dioxolane (DAPD), famciclovir, penciclovir, 2-amino-1,9-dihydro-9-[4-hydroxy-3-(hydroxymethyl)-2-methylenecyclo-pentyl]-6H-purin-6-one (entecavir, BMS-200475), 9-[2-(phosphono-methoxy)ethyl]-adenine (PMEA, adefovir, dipivoxil); 9-((1R,2R,3S)-2,3-bis (hydroxymethyl)cyclo-butyl)guanine (lobucavir), ganciclovir, and ribavirin.

70. The phannaceutical composition according to claim 43, wherein the anti-hepatitis agent is β-L-2-hydroxymethyl-5-(cytosin-1-yl)-1,3-oxathiolane (3TC).

71. The pharmaceutical composition according to claim 43, wherein the anti-hepatitis agent is cis-2-hydroxymethyl-5-(5-fluorocytosin-1-yl)-1,3-oxathiolane (FTC).

72. The pharmaceutical composition according to claim 43, wherein the anti-hepatitis agent is L-2'-fluoro-5-methyl-arabinofuranosyluridine (L-FMAU).

73. The pharmaceutical composition according to claim 43, wherein the anti-hepatitis agent is β-D-2,6-diaminopurine dioxolane (DAPD).

74. The pharmaceutical composition according to claim 43, wherein the anti-hepatitis agent is famicilovir.

75. The pharmaceutical composition according to claim 43, wherein the anti-hepatitis agent is penciclovir.

76. The pharmaceutical composition according to claim 43, wherein the anti-hepatitis agent is 2-amino-1,9dihydro-9-[4-hydroxy-3-(hydroxymethyl)-2-methylene-cyclopentyl]-6H-purin-6-one (entecavir, BMS-200475).

77. The pharmaceutical composition according to claim 43, wherein the anti-hepatitis agent is 9-[2-(phosphono-methoxy)ethy]-adenine (PMEA, adefovir, dipivoxil).

78. The pharmaceutical composition according to claim 43, wherein the anti-hepatitis agent is 9-((1R,2R,3S)-2,3-bis (hydroxymethyl)cyclo-butyl)guanine (lobucavir).

79. The pharmaceutical composition according to claim 43, wherein the anti-hepatitis agent is ganciclovir.

80. The pharmaceutical composition according to claim 43, wherein the anti-hepatitis agent is ribavirin.

81. The method of claim 20, wherein the β-L-nucleoside is

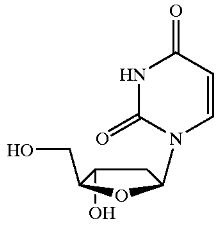

or a pharmaceutically acceptable salt thereof.

* * * * *